United States Patent
Naruse et al.

(10) Patent No.: US 10,578,854 B2
(45) Date of Patent: Mar. 3, 2020

(54) OPTICAL CONNECTOR, OPTICAL CONNECTOR SET, IMAGE PICKUP UNIT, IMAGE PICKUP SYSTEM, AND OPTICAL TRANSMISSION MODULE

(71) Applicant: SONY CORPORATION, Tokyo (JP)

(72) Inventors: Terukazu Naruse, Kanagawa (JP); Tsuyoshi Ogawa, Kanagawa (JP); Kazuyoshi Yamada, Tokyo (JP)

(73) Assignee: SONY CORPORATION, Tokyo (JP)

( * ) Notice: Subject to any disclaimer, the term of this patent is extended or adjusted under 35 U.S.C. 154(b) by 93 days.

(21) Appl. No.: 15/554,777

(22) PCT Filed: Feb. 17, 2016

(86) PCT No.: PCT/JP2016/000838
§ 371 (c)(1),
(2) Date: Aug. 31, 2017

(87) PCT Pub. No.: WO2016/147556
PCT Pub. Date: Sep. 22, 2016

(65) Prior Publication Data
US 2018/0239124 A1    Aug. 23, 2018

(30) Foreign Application Priority Data

Mar. 17, 2015   (JP) .................................. 2015-053827
Mar. 30, 2015   (JP) .................................. 2015-068337

(51) Int. Cl.
*G02B 23/24* (2006.01)
*G02B 6/32* (2006.01)
(Continued)

(52) U.S. Cl.
CPC ...... *G02B 23/2446* (2013.01); *A61B 1/00096* (2013.01); *A61B 1/00117* (2013.01);
(Continued)

(58) Field of Classification Search
CPC .................. G02B 23/2446; A61B 1/00126
See application file for complete search history.

(56) References Cited

U.S. PATENT DOCUMENTS

| | | | |
|---|---|---|---|
| 2002/0037142 A1* | 3/2002 | Rossi | G02B 6/4204 385/92 |
| 2002/0135912 A1* | 9/2002 | Ryall | G02B 6/2937 359/892 |
| 2010/0104244 A1* | 4/2010 | Grinderslev | G02B 6/32 385/74 |

FOREIGN PATENT DOCUMENTS

| | | |
|---|---|---|
| JP | 04-128812 A | 4/1992 |
| JP | 2000-262463 A | 9/2000 |

(Continued)

OTHER PUBLICATIONS

International Search Report and Written Opinion of PCT Application No. PCT/JP2016/000838, dated May 17, 2016, 03 pages of English Translation and 09 pages of ISRWO.

*Primary Examiner* — Omar R Rojas
(74) *Attorney, Agent, or Firm* — Chip Law Group

(57) ABSTRACT

[Object] To provide an optical connector and an optical connector set which are excellent in environment resistance and suitable for the use in medical instruments, an image pickup unit and an image pickup system that use the optical connector, and an optical transmission module. [Solving Means] An optical connector according to the present technology includes a lens support, a fiber ferrule, a lens, and a lens retainer. The lens support includes a through-hole. An optical fiber is connected to the fiber ferrule. The fiber ferrule is press-fitted in the through-hole. The lens is inserted into the through-hole. The lens retainer is press-fitted in the lens support and sandwiches the lens between the lens retainer and the fiber ferrule.

9 Claims, 28 Drawing Sheets

(51) Int. Cl.
    *A61B 1/04*     (2006.01)
    *G02B 6/42*     (2006.01)
    *G02B 6/38*     (2006.01)
    *A61B 1/00*     (2006.01)
    *A61B 1/07*     (2006.01)
    *A61B 1/05*     (2006.01)
    *H04N 7/22*     (2006.01)
    *A61B 1/06*     (2006.01)
    *H04N 5/225*     (2006.01)

(52) U.S. Cl.
    CPC ...... *A61B 1/00126* (2013.01); *A61B 1/00195* (2013.01); *A61B 1/04* (2013.01); *A61B 1/05* (2013.01); *A61B 1/07* (2013.01); *G02B 6/32* (2013.01); *G02B 6/38* (2013.01); *G02B 6/42* (2013.01); *H04N 7/22* (2013.01); *A61B 1/0661* (2013.01); *G02B 6/3825* (2013.01); *G02B 6/3869* (2013.01); *G02B 6/4246* (2013.01); *G02B 6/4292* (2013.01); *H04N 5/2251* (2013.01); *H04N 2005/2255* (2013.01)

(56) References Cited

FOREIGN PATENT DOCUMENTS

JP      2004-147032 A      5/2004
JP      2004-239970 A      8/2004

* cited by examiner

OPTICAL CONNECTOR, OPTICAL CONNECTOR SET, IMAGE PICKUP UNIT, IMAGE PICKUP SYSTEM, AND OPTICAL TRANSMISSION MODULE

CROSS REFERENCE TO RELATED APPLICATIONS

This application is a U.S. National Phase of International Patent Application No. PCT/JP2016/000838 filed on Feb. 17, 2016, which claims priority benefit of Japanese Patent Application No. JP 2015-053827 filed in the Japan Patent Office on Mar. 17, 2015 and also claims priority benefit of Japanese Patent Application No. JP 2015-068337 filed in the Japan Patent Office on Mar. 30, 2015. Each of the above-referenced applications is hereby incorporated herein by reference in its entirety.

TECHNICAL FIELD

The present technology relates to an optical connector and an optical connector set that can be used for optical communication of medical instruments, to an image pickup unit and an image pickup system that use the optical connector, and to an optical transmission module.

BACKGROUND ART

An endoscope is constituted of an image pickup distal end and a main body. The image pickup distal end includes an optical system and an image pickup device and is inserted into the body of a patient. The main body is placed outside the body and operates the image pickup distal end and acquires picked-up images. Conventionally, electrical signals have been used for communication (image transmission, etc.) between the image pickup distal end and the main body (e.g., see Patent Literature 1).

The image pickup distal end has to be detached from the main body for each surgical operation and subjected to sterilization treatment. Therefore, the main body and the image pickup distal end are connected to each other through an easily attachable/detachable connector. Here, the transmission capacity has increased because of improvements in the resolution of the endoscope, and hence the use of optical communication for the communication between the image pickup distal end and the main body has been studied.

An endoscope for medical purposes includes an insertion portion incorporating therein an image pickup device such as CCD and CMOS image sensors. By inserting the insertion portion into a body, organs inside body cavities and lesions can be observed (e.g., see Patent Literature 1). In recent years, an image pickup device having a large number of pixels, which enables higher resolution image observation to be performed, has been developed and the use of the image pickup device having a large number of pixels in the endoscope has been studied.

In a case of using the image pickup device having a large number of pixels in the endoscope, it is necessary to incorporate an optical transmission module in the endoscope in order to speedily transmit image signals between the image pickup device and a signal processing apparatus. Electrical signals of an image generated by the image pickup device are converted into optical signals at the optical transmission module and transmitted to the signal processing apparatus via an optical fiber.

CITATION LIST

Patent Literature

Patent Literature 1: Japanese Patent Application Laid-open No. 2000-262463

DISCLOSURE OF INVENTION

Technical Problem

However, adhesion fixing is often used in currently prevailing connectors for optical communication (hereinafter, optical connectors). Therefore, in a high load environment, for example, sterilization treatment (cleansing treatment at high temperature, high humidity, high pressure), deterioration in durability due to the humidity and deterioration in characteristics due to thermal expansion easily occur, which are problematic from the perspective of the reliability. Optical connectors usable not only in endoscopes but also in various medical instruments exposed to such a high load environment are desirable.

In view of the above-mentioned circumstances, it is an object of the present technology to provide an optical connector and an optical connector set which are excellent in environment resistance and suitable for the use in medical instruments and an image pickup unit and an image pickup system that use the optical connector.

Further, after a surgery, the endoscope has to be subjected to sterilization treatment (autoclave treatment) at high temperature and high humidity. The sterilization treatment is conducted in a pressurized, high humidity environment where the temperature is 100° C. or more and the atmospheric pressure is at 1 atm or more. Meanwhile, the endoscope is subjected to sterilization treatment approximately several hundreds to several thousands of times. Therefore, it is desirable for the optical transmission module to have a high environment resistance which enables it to be resistant against a temperature cycle of the plurality of times of sterilization treatment and preservation at high temperature and high humidity. In particular, optical devices installed in the optical transmission module are easily deteriorated in a high temperature and high humidity environment, and hence need to be protected.

In view of the above-mentioned circumstances, it is an object of the present technology to provide an optical transmission module having a high environment resistance.

Solution to Problem

In order to accomplish the above-mentioned objects, an optical connector according to an embodiment of the present technology includes a lens support, a fiber ferrule, a lens, and a lens retainer.

The lens support includes a through-hole.

An optical fiber is connected to the fiber ferrule. The fiber ferrule is press-fitted in the through-hole.

The lens is inserted into the through-hole.

The lens retainer is press-fitted in the lens support and sandwiches the lens between the lens retainer and the fiber ferrule.

With this configuration, the lens and the lens retainer are joined to each other by being press-fitted in the lens support, and hence the use of adhesives is unnecessary. Therefore, the optical connector has a high environment resistance. Even if it is under a sterilization treatment (high temperature, high humidity, high pressure) condition, deterioration in fixation strength and deterioration in characteristics such as positional errors hardly occur. Thus, it is suitable for the use in medical instruments.

The optical connector may further include a connector frame in which the lens support is press-fitted and which is fitted in/on a connection target connector.

Also in this configuration, the lens support is press-fitted in the connector frame, and hence an optical connector having a high environment resistance can be achieved. By providing the lens support and the connector frame as separate members, the shape of the connector frame can be simplified in comparison with a case where the both members are an identical member, and a high workability is not required for fabricating the connector frame.

The lens support may be a connector frame fitted in/on a connection target connector.

The lens support can also be used as the connector frame. The lens support and the connector frame are not separate members. Therefore, assembly simplification due to the reduced number of components and improvements in positional errors due to component tolerance and the like become possible.

The lens retainer may be made of a material not having light transmissivity and include an opening that permits emitted light of the lens to pass therethrough.

By providing the lens retainer with the opening, an optically opaque material can be employed as the material of the lens retainer and it becomes possible to use a material (stainless steel, ultra-hard metal, etc.) excellent in the environment resistance.

The lens support may include a recess portion that communicates with the through-hole, and the lens retainer may be press-fitted in the recess portion.

The lens retainer is press-fitted in the recess portion and sandwiches, between the lens retainer and the fiber ferrule, the lens inserted into the through-hole that communicates with the recess portion.

In order to accomplish the above-mentioned objects, an optical connector set according to an embodiment of the present technology includes a first optical connector and a second optical connector.

The first optical connector includes a first lens support including a first through-hole, a first fiber ferrule to which a first optical fiber is connected and which is press-fitted in the first through-hole, a first lens which is inserted into the first through-hole and which emitted light of the first optical fiber enters, and a first lens retainer which is press-fitted in the first lens support and sandwiches the first lens between the first lens retainer and the first fiber ferrule.

The second optical connector includes a second lens support including a second through-hole, a second fiber ferrule to which a second optical fiber is connected and which is press-fitted in the second through-hole, a second lens which is inserted into the second through-hole and causes emitted light to enter the second optical fiber, and a second lens retainer which is press-fitted in the second lens support and sandwiches the second lens between the second lens retainer and the second fiber ferrule, in which The first optical connector and the second optical connector are attachable/detachable, and emitted light of the first lens enters the second lens once the first optical connector and the second optical connector are connected to each other.

In order to accomplish the above-mentioned objects, an image pickup unit according to an embodiment of the present technology includes an image pickup portion, a cable, and an optical connector.

The image pickup portion includes an image pickup device, and a photoelectric conversion device that converts an output signal of the image pickup device into an optical signal.

The cable is connected to the photoelectric conversion device and includes an optical fiber which the optical signal enters.

The optical connector includes a lens support including a through-hole, a fiber ferrule to which the optical fiber is connected and which press-fitted in the through-hole, a lens which is inserted into the through-hole and which emitted light of the optical fiber enters, and a lens retainer which is press-fitted in the lens support and sandwiches the lens between the lens retainer and the fiber ferrule.

In order to accomplish the above-mentioned objects, an image pickup system according to an embodiment of the present technology includes an image pickup unit and a main body unit.

The image pickup unit includes an image pickup unit, a cable, and a first optical connector.

The image pickup portion includes an image pickup device, and a first photoelectric conversion device that converts an output signal of the image pickup device into an optical signal.

The cable is connected to the first photoelectric conversion device and includes a first optical fiber which the optical signal enters.

The optical connector includes a first lens support including a first through-hole, a first fiber ferrule to which a first optical fiber is connected and which is press-fitted in the first through-hole, a first lens which is inserted into the first through-hole and which emitted light of the first optical fiber enters, and a first lens retainer which is press-fitted in the first lens support and sandwiches the first lens between the first lens retainer and the first fiber ferrule.

The main body unit includes a second optical connector and a second photoelectric conversion device.

The second optical connector is detachably connected to the first optical connector. The optical signal is transferred to the second optical connector.

The second photoelectric conversion device converts the optical signal into an electrical signal.

The second optical connector includes a second lens support including a second through-hole, a second fiber ferrule to which a second optical fiber is connected and which is press-fitted in the second through-hole, a second lens which is inserted into the second through-hole and causes emitted light to enter the second optical fiber, and a second lens retainer which is press-fitted in the second lens support and sandwiches the second lens between the second lens retainer and the second fiber ferrule. Emitted light of the first lens enters the second lens once the second optical connector is connected to the first optical connector.

In order to accomplish the above-mentioned objects, an optical transmission module according to an embodiment of the present technology includes a first substrate, a second substrate, an optical fiber, a light-emitting device, and a shield case.

The second substrate is fixed to the first substrate and includes a wire electrically connected to the first substrate and a through-hole.

The optical fiber is inserted into the through-hole and fixed to the second substrate through a first synthetic resin.

The light-emitting device is mounted on the second substrate, includes a light-emitting portion opposed to an end portion of the optical fiber, and is electrically connected to the wire.

The shield case is joined to the first substrate and forms a housing space surrounding components installed in the first substrate, the components including the second substrate and the light-emitting device.

With this configuration, the light-emitting device and the optical fiber are optically coupled to each other directly with a simple structure. With this, an optical coupling change with respect to a temperature cycle of an autoclave in sterilization treatment or the like is reduced, which makes the transmission of optical signals stable. Further, the difference in coefficient of thermal expansion between the light-emitting device and the second substrate can be reduced. Thus, a high reliability of electrical connection can be ensured therebetween.

The optical transmission module may further include a sealing resin which is made of a second synthetic resin and seals the shield case.

With this configuration, the sealing resin prevents moisture from infiltrating the housing space, and it becomes possible to protect the various components inside the housing space from the high temperature and high humidity environment. In particular, the light-emitting device is weak to the high temperature and high humidity environment. However, by protecting the light-emitting device from the high temperature and high humidity environment, it is possible to increase the reliability of the optical transmission module.

The light-emitting device may be mounted on the second substrate through a connection bump.

By mounting the light-emitting device on the second substrate through the connection bump, that is, by flip-chip mounting, it becomes easy for heat generated in the light-emitting device to be transferred to the second substrate, and it is possible to increase the reliability of the optical transmission module.

The first substrate and the second substrate may be made of silicon, quartz, glass, ceramics, or organic materials.

The connection bump may be made of solder or gold.

The second synthetic resin may be an epoxy-based resin or a silicone-based resin.

The epoxy-based resin and the silicone-based resin have a low permeability to moisture. By using the epoxy-based resin or the silicone-based resin as the sealing resin, it is possible to prevent moisture from infiltrating the housing space.

The shield case may include an opening. The optical fiber may be inserted into the housing space through the opening. The optical transmission module may further include: a shield receiver which is arranged on the first substrate and in/on which the shield case is fitted, the shield receiver being arranged surrounding the components installed in the first substrate; and a cover portion which is made of the second synthetic resin or a third synthetic resin and closes a gap between the opening and the shield receiver.

With this configuration, the gap between the opening and the shield receiver is closed by the cover portion. Thus, it is possible to prevent the sealing resin from flowing into the housing space.

Advantageous Effects of Invention

As described above, in accordance with the present technology, it is to provide an optical connector and an optical connector set which are excellent in environment resistance and suitable for the use in medical instruments and an image pickup unit and an image pickup system that use the optical connector.

Further, as described above, in accordance with the present technology, it is possible to provide an optical transmission module having a high environment resistance. It should be noted that the effects described here are not necessarily limitative and any effect described in the present disclosure may be provided.

MODE(S) FOR CARRYING OUT THE INVENTION

First Embodiment

An endoscope system according to a first embodiment of the present technology will be described.

[Configuration of Endoscope System]

Figure 1:
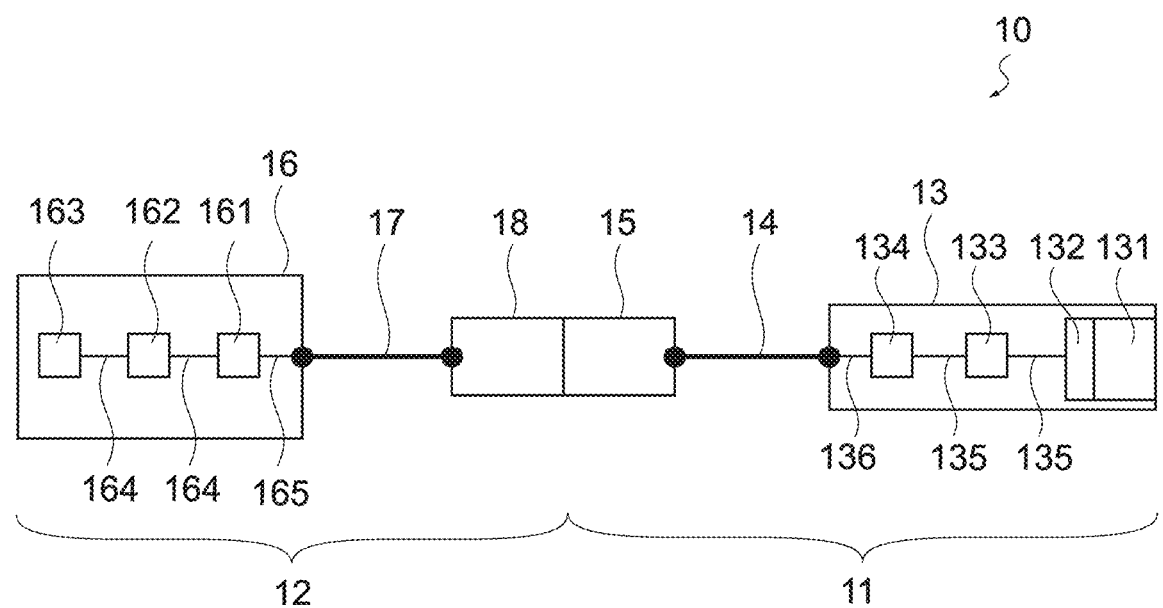
FIG. 1 A schematic view of an endoscope system according to a first embodiment of the present technology.

FIG. 1 is a schematic view showing a configuration of an endoscope system 10 according to this embodiment. As shown in the figure, an endoscope system 10 is constituted of an image pickup unit 11 and a main body unit 12.

The image pickup unit 11 includes an image pickup distal end 13, a cable 14, and a plug-side connector 15. The image pickup unit 11, which is a distal end of the endoscope, is a portion to be inserted into the body of a patient.

The image pickup distal end 13 includes an image pickup optical system 131, an image pickup device 132, a signal processing unit 133, and a photoelectric conversion device 134. The image pickup device 132, the signal processing unit 133, and the photoelectric conversion device 134 are connected to one another through signal wires 135. The photoelectric conversion device 134 is connected to optical fibers 136.

When an image is picked up by the image pickup device 132 via the image pickup optical system 131, generated image signals are transferred to the photoelectric conversion device 134 via the signal processing unit 133 and the signal wires 135 and converted into optical signals by the photoelectric conversion device 134. The photoelectric conversion device 134 outputs the converted optical signals to the optical fibers 136.

The configuration of the image pickup distal end 13 is not particularly limited and it only needs to include at least the image pickup device and the photoelectric conversion device. For example, the image pickup distal end 13 may be provided with an illumination optical system for image pickup and the like.

The cable 14 includes the optical fibers 136 and transfers optical signals to the plug-side connector 15 from the image pickup distal end 13. The cable 14 can be inserted into an outer cylindrical tube (not shown). In addition to the optical fibers 136, the cable 14 may be provided with a wire for supplying electric power and a wire for control signals from the main body unit 12 to the image pickup distal end 13.

The plug-side connector 15 is detachably connected to a receptor-side connector 18 to be described later and sends optical signals to the receptor-side connector 18. The plug-side connector 15 will be described later in detail.

The image pickup unit 11 has the configuration as described above. Once the connection of the plug-side connector 15 and the receptor-side connector 18 is cancelled, the image pickup unit 11 can be detached from the main body unit 12.

The main body unit 12 includes a main body 16, a cable 17, and the receptor-side connector 18. The main body unit 12 is a portion that is placed outside the body of the patient, is operated by a surgeon, and acquires images picked up by the image pickup distal end 13.

The main body 16 includes a photoelectric conversion device 161, a signal processing unit 162, and an image generating unit 163. The photoelectric conversion device 161, the signal processing unit 162, and the image generating unit 163 are connected to one another through signal wires 164 and the photoelectric conversion device 161 is connected to optical fibers 165.

The photoelectric conversion device 161 converts optical signals output from the optical fibers 165 into electrical signals and supplies them to the image generating unit 163 via the signal wires 164 and the signal processing unit 162. The image generating unit 163 generates an image from the supplied electrical signals and displays it on a display (not shown) provided in the main body 16 or outputs it to an external apparatus connected to the main body 16.

The configuration of the main body 16 is not particularly limited and it only needs to include at least the photoelectric conversion device. For example, the main body 16 may be provided with an input switch and the like for surgeon's operations (e.g., operations to bend and stretch the outer cylindrical tube).

The cable 17 includes the optical fibers 165 and transfers optical signals to the main body 16 from the receptor-side connector 18. In addition to the optical fibers 165, the cable 17 may be provided with a wire for supplying electric power and a wire for control signals to the image pickup unit 11 from the main body 16.

The receptor-side connector 18 is detachably connected to the plug-side connector 15 and receives optical signals from the plug-side connector 15. The receptor-side connector 18 will be described later in detail.

The main body unit 12 has the configuration as described above. Note that the main body unit 12 does not necessarily need to include the cable 17 and the main body 16 may be directly provided with the receptor-side connector 18. In this case, the receptor-side connector 18 and the photoelectric conversion device 161 can be connected to each other through the optical fibers 165 arranged within the main body 16.

[Structure of Optical Connector]

Figure 2:
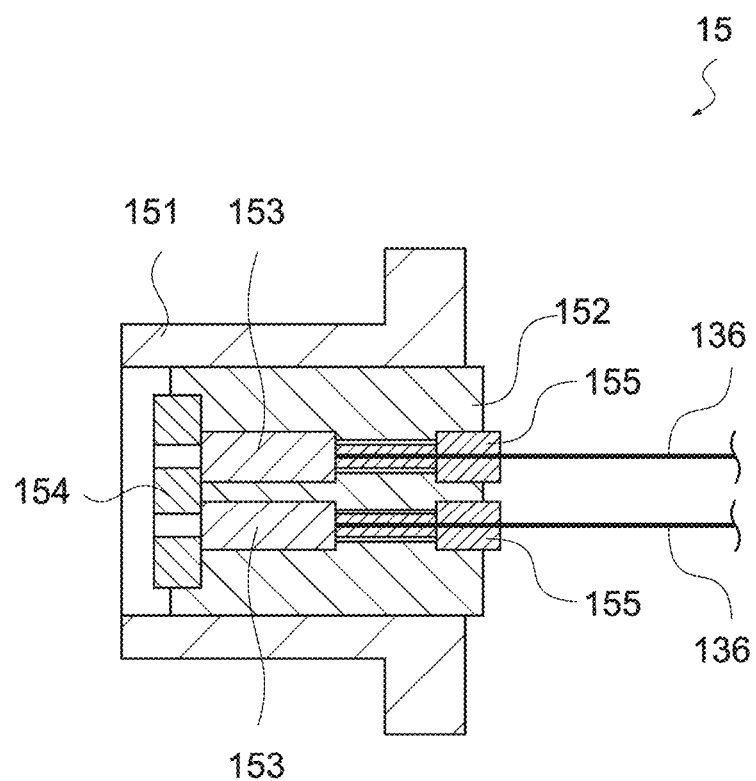
FIG. 2 A cross-sectional view of a plug-side connector of the endoscope system.
Figure 3:
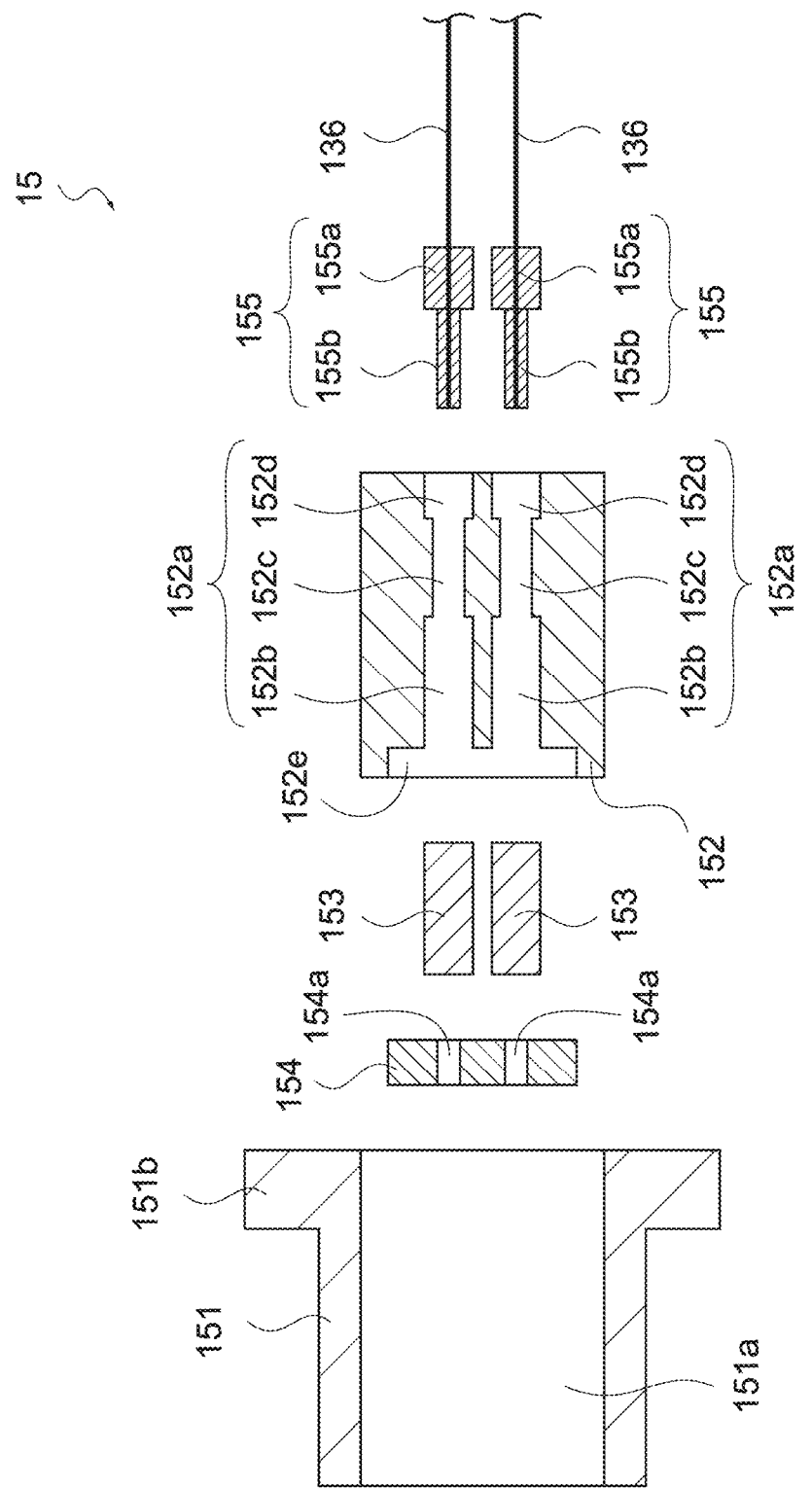
FIG. 3 An exploded view of the plug-side connector of the endoscope system.
Figure 4:
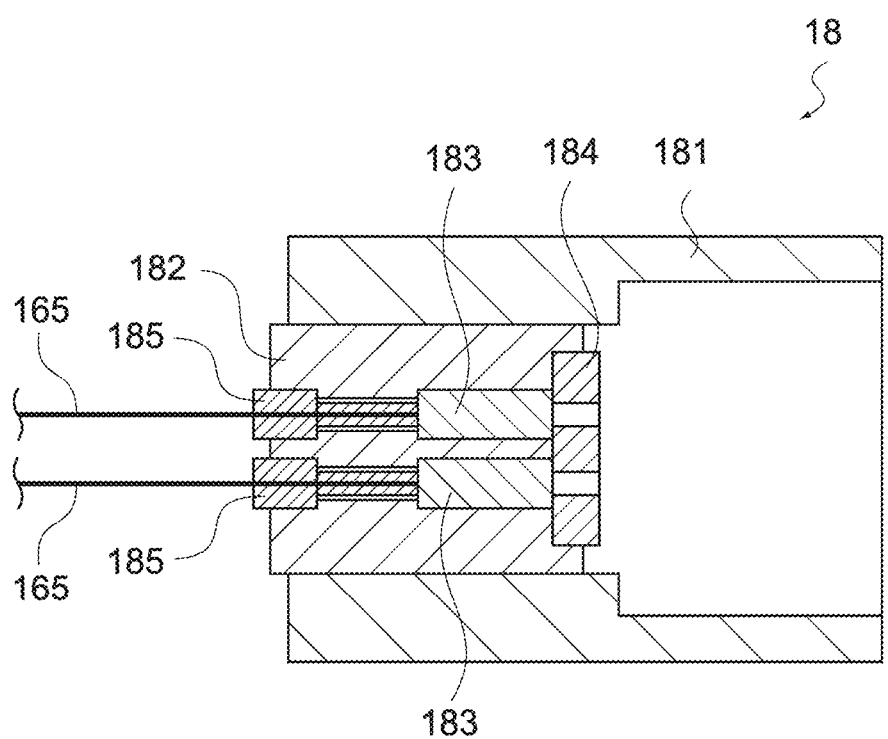
FIG. 4 A cross-sectional view of a receptor-side connector of the endoscope system.
Figure 5:
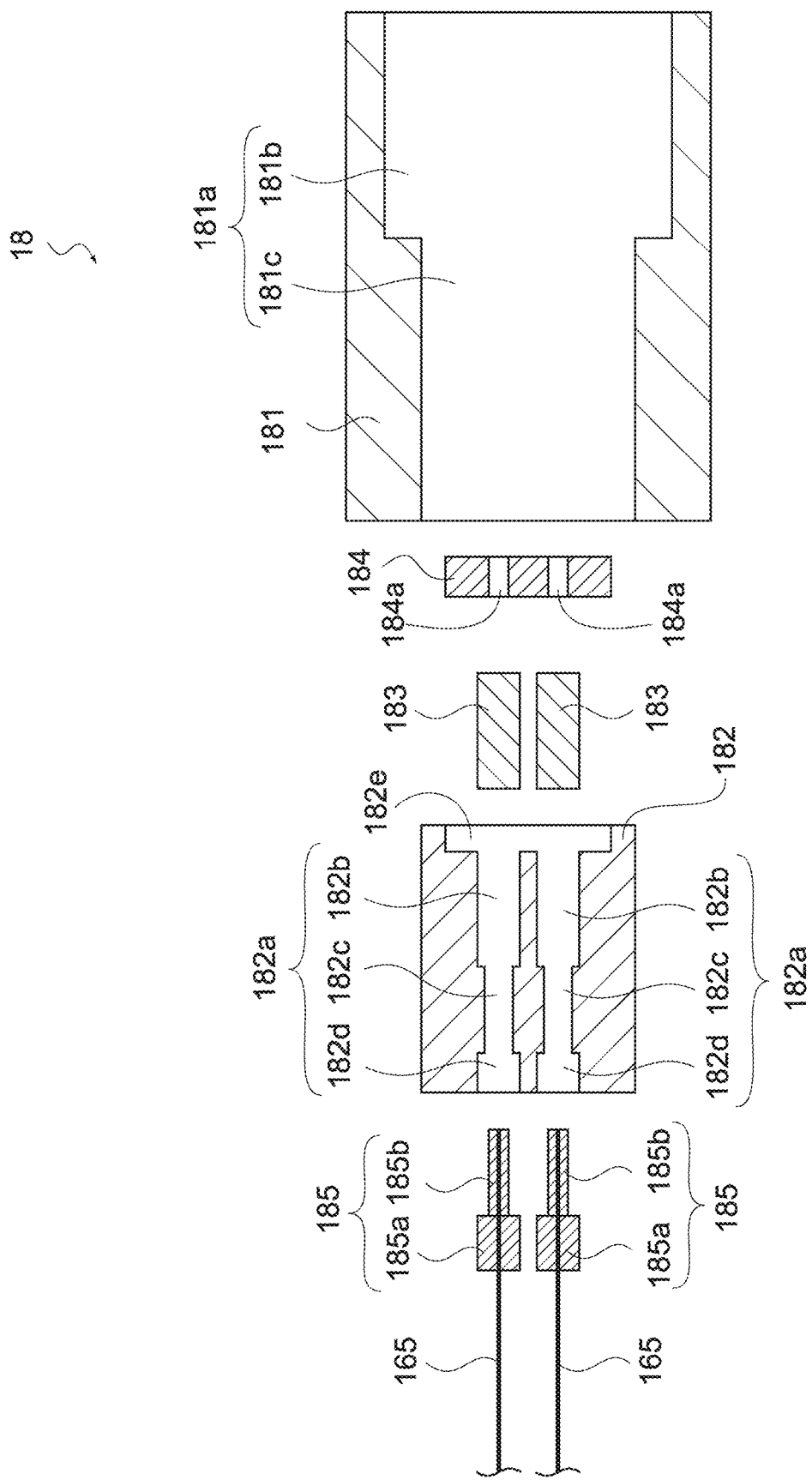
FIG. 5 An exploded view of the receptor-side connector of the endoscope system.
Figure 6:
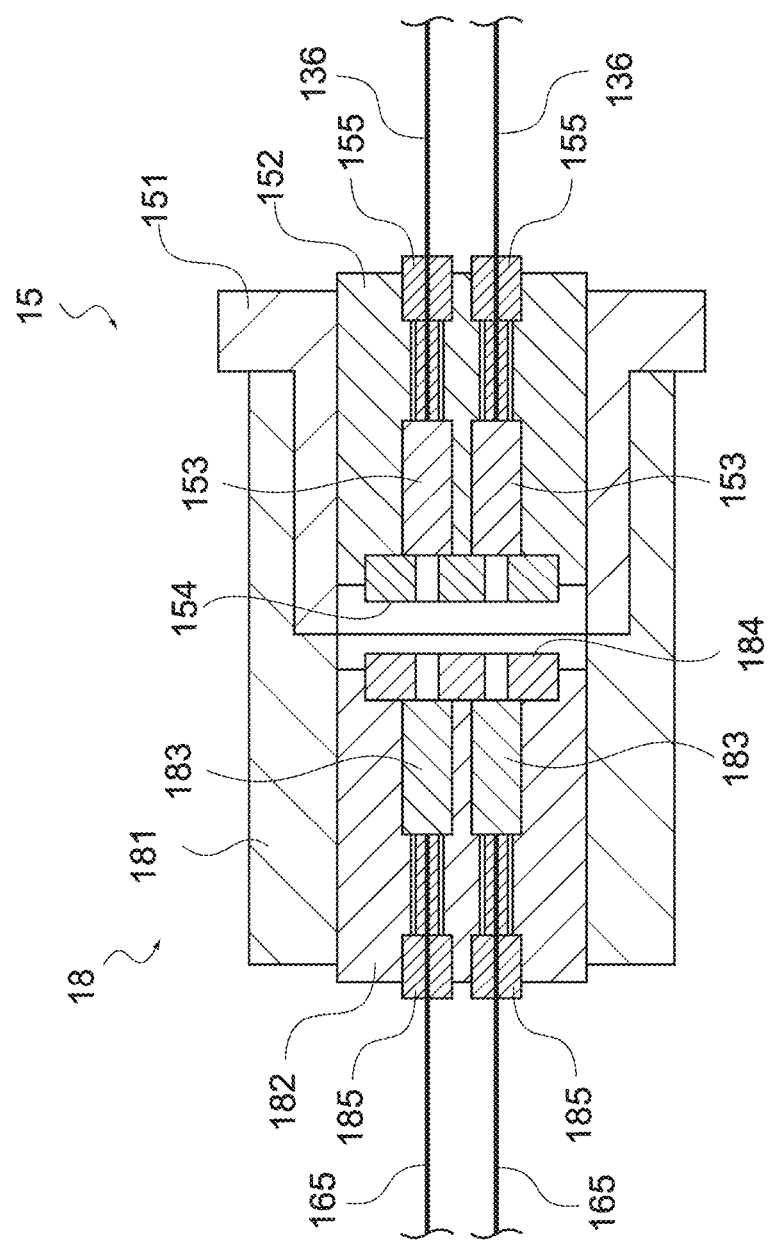
FIG. 6 A cross-sectional view showing a state of connection between the plug-side connector and the receptor-side connector of the endoscope system.

The plug-side connector 15 and the receptor-side connector 18 will be described. FIG. 2 is a cross-sectional view of the plug-side connector 15. FIG. 3 is an exploded view of the plug-side connector 15. FIG. 4 is a cross-sectional view of the receptor-side connector 18. FIG. 5 is an exploded view of the receptor-side connector 18. FIG. 6 is a cross-sectional view showing a state in which the plug-side connector 15 and the receptor-side connector 18 are connected to each other.

As shown in FIGS. 2 and 3, the plug-side connector 15 is constituted of a connector frame 151, a lens holder 152, lenses 153, a lens retainer 154, fiber ferrules 155, and the optical fibers 136.

Figure 7:
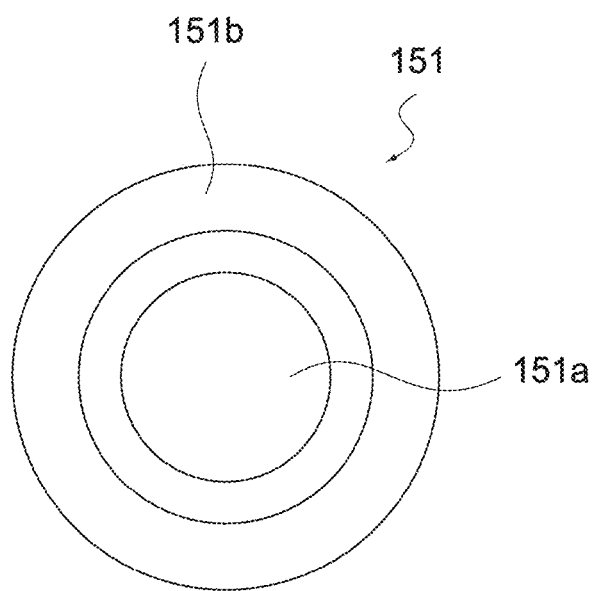
FIG. 7 A plan view of a connector frame of the plug-side connector of the endoscope system.

The connector frame 151 is, as shown in FIG. 6, a member fitted in the connector frame 181 of the receptor-side connector 18. FIG. 7 is a plan view of the connector frame 151 and is a view as the connector frame 151 is viewed in the direction of the distal end (direction opposite to the optical fibers 136).

As shown in FIGS. 3 and 7, the connector frame 151 has a cylindrical shape including a through-hole 151a and a projection 151b is provided in an outer circumferential surface thereof. When the connector frame 151 is fitted in the connector frame 181, the projection 151b comes into contact with the connector frame 181 and defines the position of the plug-side connector 15 with respect to the receptor-side connector 18. Note that the connector frame 151 is not limited to that cylindrical shape and only needs to have a shape that can be fitted in the connector frame 181.

Although the material of the connector frame 151 is not particularly limited, a material excellent in environment resistance (thermal resistance, humidity resistance, pressure resistance, etc.) and having elasticity suitable for fitting in the connector frame 181 is favorable. Specifically, the connector frame 151 can be made of stainless steel, aluminum, or zirconia. Further, the connector frame 151 may be made of a plated metal material, for example, may be made of a brass base material plated with Ni.

Figure 8:
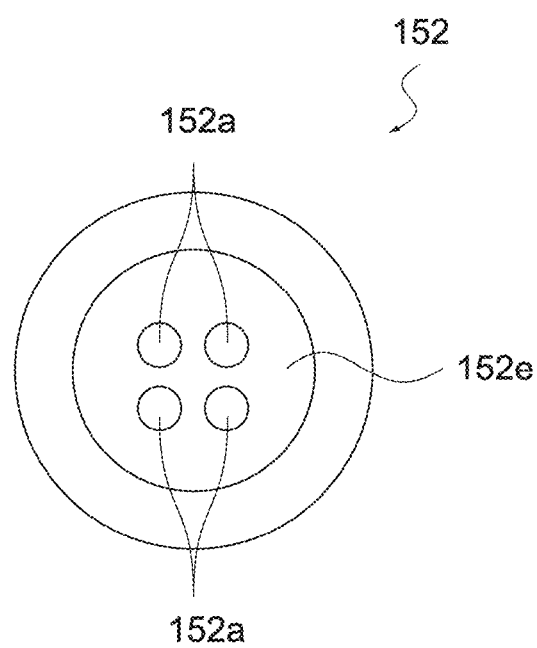
FIG. 8 A plan view of a lens holder of the plug-side connector of the endoscope system.

The lens holder 152 is press-fitted in the through-hole 151a of the connector frame 151 and supports the lenses 153, the lens retainer 154, and the fiber ferrules 155. FIG. 8 is a view as the lens holder 152 is viewed in the direction of the distal end. As shown in FIGS. 3 and 8, the lens holder 152 has a columnar shape. Note that the lens holder 152 is not limited to the columnar shape and only needs to have a shape that can be press-fitted in the through-hole 151a.

Further, the lens holder 152 includes the through-holes 152a. The number of through-holes 152a is identical to the number of optical fibers 136 connected to the plug-side connector 15. Hereinafter, although descriptions will be made assuming that the number of optical fibers 136 is 4, it does not need to be 4 and the number of through-holes 152a can also be appropriately changed in a manner that depends on the number of optical fibers 136.

As shown in FIG. 3, the through-hole 152a is constituted of a first hole portion 152b, a second hole portion 152c, and a third hole portion 152d. The second hole portion 152c is a portion having a smaller diameter than that of each of the first hole portion 152b and the third hole portion 152d. The diameter of each of the first hole portion 152b and the third hole portion 152d can be, for example, 2.04 mm. Note that the diameter of the first hole portion 152b and the diameter of the third hole portion 152d do not need to be the same.

Further, the lens holder 152 includes a recess portion 152e. As shown in FIGS. 3 and 8, the recess portion 15e is formed continuously with the first hole portions 152b. The recess portion 152e can have a disk-like, recess-like shape, though not limited thereto.

Although the material of the lens holder 152 is not particularly limited, a material excellent in the environment resistance is favorable. Specifically, the lens holder 152 can be made of stainless steel, aluminum, or zirconia. Further, the lens holder 152 may be made of a plated metal material, for example, may be made of a brass base material plated with Ni.

The lenses 153 are inserted into the first hole portions 152b of the through-holes 152a and convert optical paths of light output from the optical fibers 136. Specifically, the lenses 153 are collimate lenses and can enlarge and collimate light emitted from the optical fibers 136. The lenses 153 can each have a columnar shape, for example, and a diameter of, for example, 2.00 mm.

One lens 153 can be arranged for each through-hole 152a, that is, a total of four lenses 153 can be arranged. However, a number of lenses 153 depending on the number of optical fibers 136 (number of through-holes 152a) connected to the plug-side connector 15 can be arranged. Each lens 153 is sandwiched and positioned by the lens retainer 154 and the fiber ferrules 155. Although the material of the lenses 153 is not particularly limited, a material excellent in the environment resistance, such as glass, is favorable.

Figure 9:
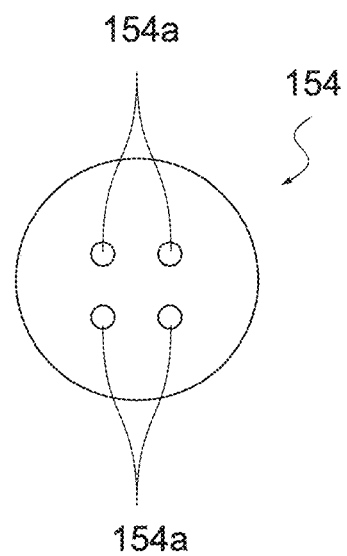
FIG. 9 A plan view of a lens retainer of the plug-side connector of the endoscope system.

The lens retainer 154 is press-fitted in the recess portion 152e of the lens holder 152 and positions the lenses 153. FIG. 9 is a plan view of the lens retainer 154 and is a view as viewed in the direction of the distal end. As shown in the figure, the lens retainer 154 includes openings 154a. The openings 154a are arranged facing the respective lenses 153 and an identical number of openings 154a to the number of lenses 153 are provided. The opening 154a has a diameter smaller than a diameter of the lens 153 and is formed in such a manner that the entire opening 154a faces the lens 153. The opening 154a can have a diameter of, for example, 1.60 mm.

The lens retainer 154 can have the disk-like shape, though not limited thereto. The lens retainer 154 only needs to have a shape conforming to the recess portion 152e. Although the material of the lens retainer 154 is not particularly limited, a material excellent in the environment resistance is favorable. Further, the openings 154a are formed in the lens retainer 154, and hence the lens retainer 154 can be made of a material not having light transmissivity. Specifically, the lens retainer 154 can be made of stainless steel, aluminum, or zirconia. Further, the lens retainer 154 may be made of a plated metal material, for example, may be made of a brass base material plated with Ni.

The fiber ferrules 155, to which the optical fibers 136 are connected, are press-fitted in the through-holes 152a. One fiber ferrule 155 is arranged for each optical fiber 136. As shown in FIG. 3, the fiber ferrule 155 includes a base portion 155a and a smaller-diameter portion 155b.

The optical fibers 136 are inserted from the base portions 155a to ends of the smaller-diameter portions 155b. As shown in FIGS. 2 and 3, the base portions 155a are press-fitted in the third hole portions 152d. The smaller-diameter portions 155b may be held in contact with inner circumferential surfaces of the second hole portions 152c or may be separated from the inner circumferential surfaces. By the fiber ferrules 155 being press-fitted in the through-holes 152a, the lenses 153 are sandwiched by the fiber ferrules 155 and the lens retainer 154 and the optical fibers 136 are held in contact with the lenses 153.

A material excellent in the environment resistance of the fiber ferrules 155 is favorable. For example, the base portions 155a can be made of stainless steel and the smaller-diameter portions 155b can be made of zirconia. The base portions 155a and the smaller-diameter portions 155b may be made of identical materials.

The optical fibers 136 are fixed in the lens holder 152 through the fiber ferrules 155 and transfer optical signals output by the photoelectric conversion device 134 (see FIG. 1) to the lenses 153. The number of optical fibers 136 is not limited to four as described above and may be three or less or five or more. Although the optical fiber 136 can have a general structure made of a glass, a synthetic resin, or the like, one excellent in the environment resistance is favorable.

Figure 10:
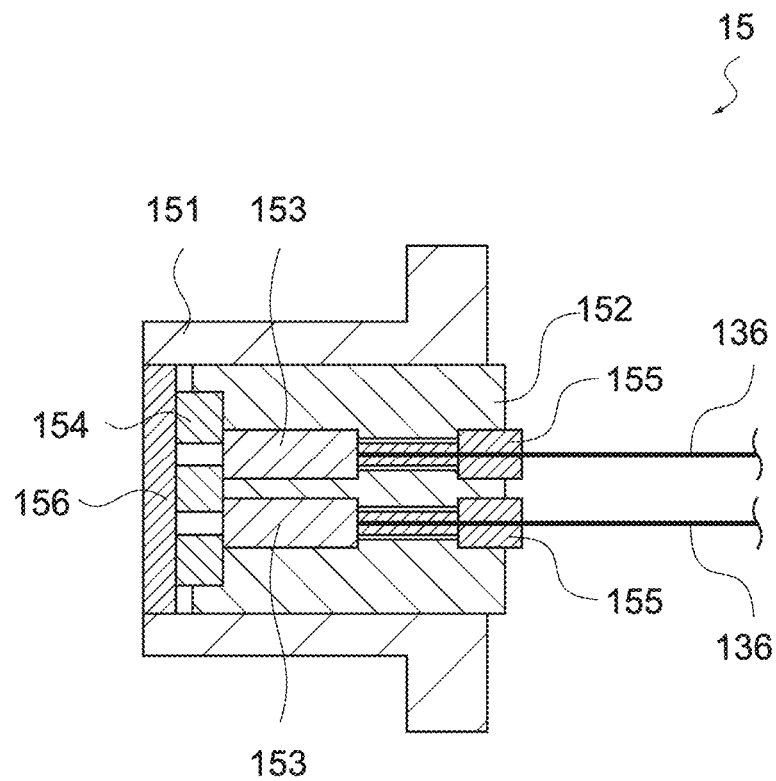
FIG. 10 A cross-sectional view showing the plug-side connector of the endoscope system.

The plug-side connector 15 has the structure as described above. Note that the structure of the plug-side connector 15 is not limited to the above-mentioned one. For example, the plug-side connector 15 may include a cover member. FIG. 10 is a cross-sectional view showing the plug-side connector 15 including a cover member 156.

As shown in the figure, the cover member 156 is fitted in the through-hole 151a of the connector frame 151 (see FIG. 3) and opposed to the lens retainer 154. The cover member 156 can be made of a light-transmissive material such as glass.

As shown in FIGS. 4 and 5, the receptor-side connector 18 is constituted of the connector frame 181, a lens holder 182, lenses 183, a lens retainer 184, fiber ferrules 185, and the optical fibers 165.

Figure 11:
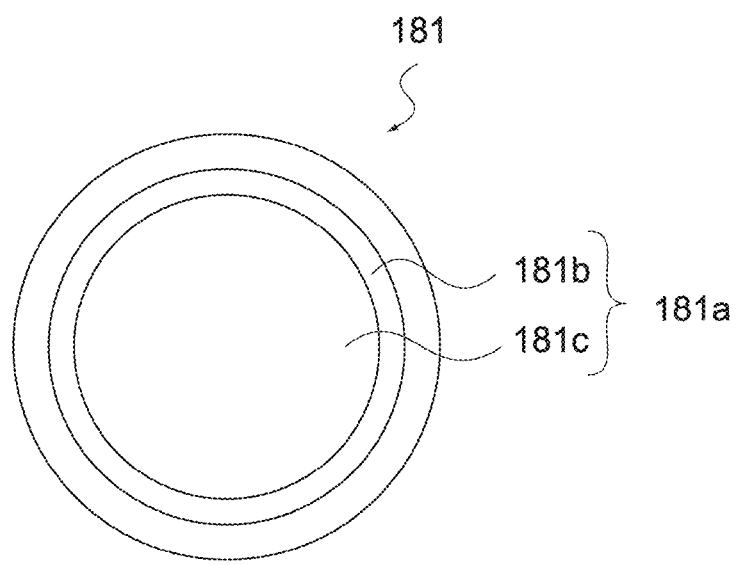
FIG. 11 A plan view of a connector frame of the receptor-side connector of the endoscope system.

The connector frame 181 is a member fitted on the connector frame 151 of the plug-side connector 15 as shown in FIG. 6. FIG. 11 is a plan view of the connector frame 181 and is a view as the connector frame 181 is viewed in the direction of the distal end (direction opposite to the optical fibers 165).

As shown in FIGS. 5 and 11, the connector frame 181 has a cylindrical shape including a through-hole 181a and the through-hole 181a is constituted of a first hole portion 181b and a second hole portion 181c. The first hole portion 181b is a portion having a diameter smaller than that of the second hole portion 181c. When the connector frame 181 is fitted on the connector frame 151, an inner circumferential surface of the first hole portion 181b is held in contact with an outer circumferential surface of the connector frame 151.

Although the material of the connector frame 181 is not particularly limited, a material excellent in the environment resistance (thermal resistance, humidity resistance, pressure resistance, etc.) and having elasticity suitable for fitting on the connector frame 151 is favorable. Specifically, the connector frame 181 can be made of stainless steel, aluminum, or zirconia. Further, the connector frame 181 may be made of a plated metal material, for example, may be made of a brass base material plated with Ni.

Configurations of the lens holder 182, the lenses 183, the lens retainer 184, and the fiber ferrules 185 can be identical to the configurations in the plug-side connector 15.

The lens holder 182 is press-fitted in the second hole portion 181c of the connector frame 181 and supports the lenses 183, the lens retainer 184, and the fiber ferrules 185. Although the lens holder 182 can have a columnar shape, the lens holder 182 only need to have a shape that can be press-fitted in the connector frame 181.

Further, the lens holder 182 includes through-holes 182a. The number of through-holes 182a is identical to the number of optical fibers 165 connected to the receptor-side connector 18 and can be appropriately changed in a manner that depends on the number of optical fibers 165. The through-hole 182a is constituted of a first hole portion 182b, a second hole portion 182c, and a third hole portion 183d. The second hole portion 182c is a portion having a smaller diameter than that of each of the first hole portion 182b and a third hole portion 182d. Each of the first hole portion 182b and the third hole portion 182d can have a diameter of, for example, 2.04 mm. Note that the diameter of the first hole portion 182b and the diameter of the third hole portion 182d do not need to be the same.

Further, the lens holder 182 includes a recess portion 182e. As shown in FIG. 5, the recess portion 182e is formed continuously with the first hole portions 182b. The recess portion 182e can have a disk-like, recess-like shape, though not limited thereto.

Although the material of the lens holder 182 is not particularly limited, a material excellent in the environment resistance is favorable. Specifically, the lens holder 182 can be made of stainless steel, aluminum, or zirconia. Further, the lens holder 182 may be made of a plated metal material, for example, may be made of a brass base material plated with Ni.

The lenses 183 are inserted into the first hole portions 182b of the through-holes 182a and convert optical paths of the entering light. Specifically, the lenses 183 are collimate lenses and can collect light entering from the lenses 153 of the plug-side connector 15 and cause it to enter the optical fibers 165. The lenses 183 can each have a columnar shape, for example, and a diameter of, for example, 2.00 mm.

One lens 183 can be arranged for each through-hole 182a, that is, a total of four lenses 183 can be arranged. However, a number of lenses 183 depending on the number of optical fibers 165 (number of through-holes 182a) connected to the receptor-side connector 18 can be arranged. Each lens 183 is sandwiched and positioned by the lens retainer 184 and the fiber ferrule 185. Although the material of the lenses 183 is not particularly limited, a material excellent in the environment resistance, such as glass, is favorable.

The lens retainer 184 is press-fitted in the recess portion 182e of the lens holder 182 and positions the lenses 183. As shown in FIG. 5, the lens retainer 184 includes openings 184a. The openings 184a are arranged facing the respective lenses 183 and an identical number of openings 184a to the number of lenses 183 are provided. The opening 184a has a diameter smaller than a diameter of the lens 183 and is formed in such a manner that the entire opening 184a faces the lens 183. The opening 184a can have a diameter of, for example, 1.60 mm.

The lens retainer 184 can have the disk-like shape, though not limited thereto. The lens retainer 184 only needs to have a shape conforming to the recess portion 182e. Although the material of the lens retainer 184 is not particularly limited, a material excellent in the environment resistance is favorable. Further, the openings 184a are formed in the lens retainer 184, and hence the lens retainer 184 can be made of a material not having light transmissivity. Specifically, the lens retainer 184 can be made of stainless steel, aluminum, or zirconia. Further, the lens retainer 184 may be made of a plated metal material, for example, may be made of a brass base material plated with Ni.

The fiber ferrules 185, to which the optical fibers 165 are connected, are press-fitted in the through-holes 182a. One fiber ferrule 185 is arranged for each optical fiber 165. As shown in FIG. 5, the fiber ferrule 185 includes a base portion 185a and a smaller-diameter portion 185b.

The optical fibers 165 are inserted from the base portions 185a to ends of the smaller-diameter portions 185b. As shown in FIGS. 4 and 5, the base portions 185a are press-fitted in the third hole portions 182d. The smaller-diameter portions 185b may be held in contact with inner circumferential surfaces of the second hole portions 182c or may be separated from the inner circumferential surfaces. By the fiber ferrules 185 being press-fitted in the through-holes 182a, the lenses 183 are sandwiched by the fiber ferrules 185 and the lens retainer 184 and the optical fibers 165 are held in contact with the lenses 183.

A material excellent in the environment resistance of the fiber ferrules 185 is favorable. For example, the base portions 185a can be made of stainless steel and the smaller-diameter portions 185b can be made of zirconia. The base portions 185a and the smaller-diameter portions 185b may be made of identical materials.

The optical fibers 165 are fixed to the lens holder 182 through the fiber ferrules 185 and transfer optical signals transferred from the plug-side connector 15 to the photoelectric conversion device 161 (see FIG. 1). The number of optical fibers 165 is not limited to four as described above and may be three or less or five or more. Although the optical fiber 165 can have a general structure made of a glass, a synthetic resin, or the like, one excellent in the environment resistance is favorable.

Figure 12:
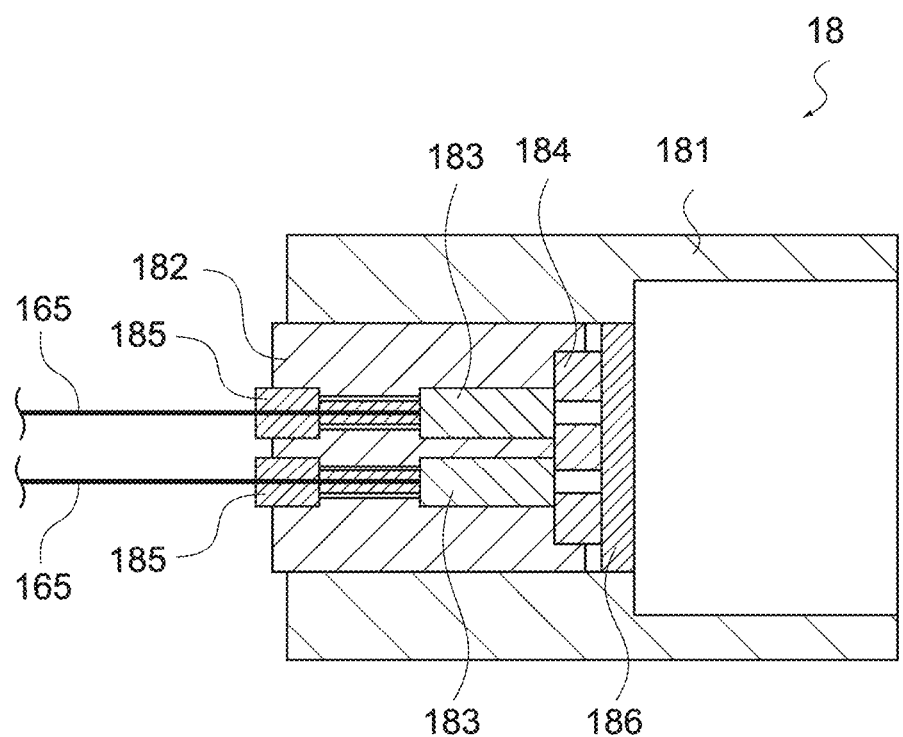
FIG. 12 A cross-sectional view showing the receptor-side connector of the endoscope system.

The receptor-side connector 18 has the structure as described above. Note that the structure of the receptor-side connector 18 is not limited to the above-mentioned one. For example, the receptor-side connector 18 may include a cover member. FIG. 12 is a cross-sectional view showing the receptor-side connector 18 including a cover member 186.

As shown in the figure, the cover member 186 is fitted in the second hole portion 181c of the connector frame 181 (see FIG. 5) and opposed to the lens retainer 184. The cover member 186 can be made of a light-transmissive material such as glass.

[Operation of Endoscope System]

An operation of the endoscope system 10 will be described. When an image is picked up by the image pickup device 132, image signals thereof are converted into optical signals by the photoelectric conversion device 134 and transferred to the optical fibers 136 (see FIG. 1).

The optical signals are emitted from the optical fibers 136 and enters the lenses 153 in the plug-side connector 15 (see FIG. 6). The lenses 153 enlarge and collimate light (optical signals) emitted from the optical fibers 136. The light emitted from the lenses 153 passes through the openings 154a (see FIG. 3) provided in the lens retainer 154 and is emitted to the receptor-side connector 18.

The light entering the receptor-side connector 18 passes through the openings 184a (see FIG. 5) provided in the lens retainer 184 and enters the lenses 183. The light entering the lenses 183 is collected by the lenses 183 and enters the optical fibers 165.

The light (optical signals) emitted from the optical fibers 165 is converted into electrical signals in the photoelectric conversion device 161 and transferred to the image generating unit 163. As described above, the image picked up at the image pickup distal end 13 is converted into the optical signals and transferred to the main body 16 via the plug-side connector 15 and the receptor-side connector 18.

The plug-side connector 15 and the receptor-side connector 18 are provided with the lenses (lenses 153 and lenses 183) and the diameter of the optical path of light transferred between the both connectors is enlarged. Therefore, high precision is not required for positioning the plug-side connector 15 and the receptor-side connector 18.

[Effects of Endoscope System]

As described above, the respective members in the plug-side connector 15 and the receptor-side connector 18 are joined to each other by press-fitting, and hence the use of adhesives is unnecessary. Therefore, the plug-side connector 15 and the receptor-side connector 18 have a high environment resistance (thermal resistance, humidity resistance, pressure resistance, etc.).

For example, in a case of performing a surgical operation using the endoscope system 10, the image pickup unit 11 to be inserted into the body of the patient has to be subjected to sterilization treatment (cleansing treatment at high temperature, high humidity, and high pressure). In the endoscope system 10, it is possible to cancel the coupling of the plug-side connector 15 and the receptor-side connector 18, separate the image pickup unit 11 from the main body unit 12, and subject the image pickup unit 11 to sterilization treatment. The plug-side connector 15 has a high environment resistance as described above. Therefore, deterioration in fixation strength and deterioration in characteristics such as positional errors, which would be caused by sterilization treatment, hardly occur and a high reliability is provided.

Modified Examples

The configuration of the endoscope system 10 is not limited to the above-mentioned one. For example, the plug-side connector 15 and the receptor-side connector 18 can also be provided with wires for electrical signals such that the plug-side connector 15 and the receptor-side connector 18 are configured to be capable of transferring electrical signals in addition to optical signals. The wires for electrical signals can be provided inside the connector frames or inside the lens holders of the both connectors. Further, the endoscope system 10 may include a connector for electrical signals other than the plug-side connector 15 and the receptor-side connector 18.

Further, the coupling mechanism of the plug-side connector 15 and the receptor-side connector 18 is also not limited to the above-mentioned configuration. In the above-mentioned configuration, the configuration in which the connector frame 151 is inserted into the connector frame 181 has been employed. However, conversely, to be specific, the connector frame 181 may be inserted into the connector frame 151.

In addition, in order to make transfer positions of optical signals between the both connectors (positions of the openings 154a and the openings 184a) correspond to each other, the shape of the connector frame 151 and the shape of the connector frame 181 may be replaced by a shape which is not a rotationally-symmetric shape (rectangular shape or polygonal shape as viewed in the direction of the distal end). The connector frame 151 and the connector frame 181 can also be provided with lock mechanisms for mutually fixing their positions.

Further, the endoscope system 10 only needs to include at least one connector having the above-mentioned configuration and either one of the plug-side connector 15 and the receptor-side connector 18 does not need to have the above-mentioned configuration.

Figure 13:
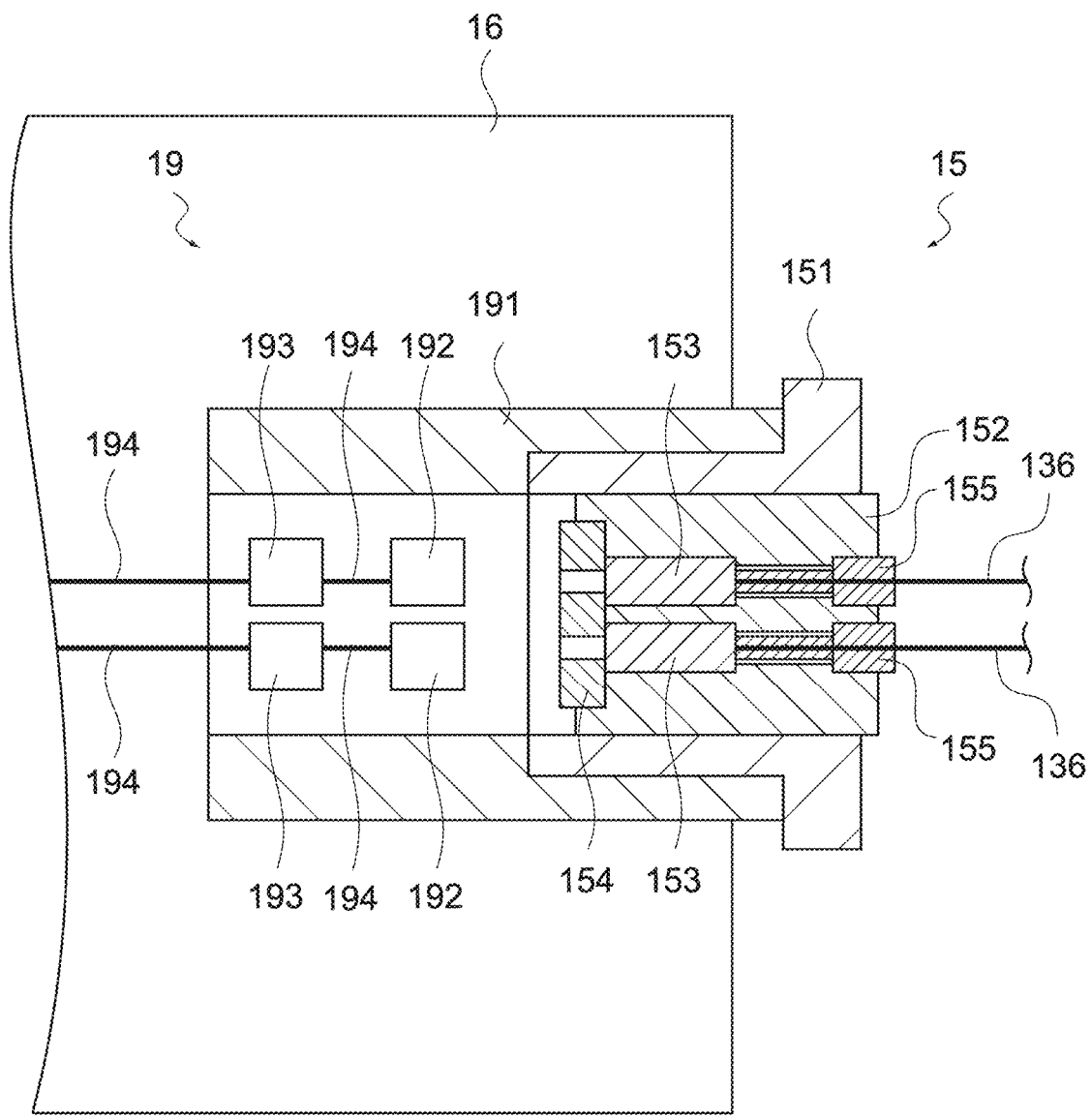
FIG. 13 A cross-sectional view of a plug-side connector and a receptor-side connector according to a modified example of the first embodiment.

FIG. 13 is a schematic view of an endoscope system 10 according to a modified example of this embodiment. This endoscope system 10 includes a plug-side connector 15 having the above-mentioned configuration and a receptor-side connector 19 having a configuration different from that of the receptor-side connector 18.

The receptor-side connector 19 can be directly provided in the main body 16 as shown in FIG. 13. However, the receptor-side connector 19 may be separated from the main body 16 and connected to the main body 16 through a cable.

The receptor-side connector 19 includes a connector frame 191, photodiodes 192, signal processing units 193, and signal wires 194.

The connector frame 191 is fitted on the connector frame 151 of the plug-side connector 15 and can have a configuration identical to that of the connector frame 181. The photodiodes 192 are provided at positions opposed to the openings 154a of the plug-side connector 15 and detect light emitted from the openings 154a and generate electrical signals.

The signal wires 194 connect the photodiodes 192, the signal processing units 193, and the image generating unit 163 to one another (see FIG. 1) and transfer electrical signals output from the photodiodes 192, to the image generating unit 163 via the signal processing unit 162.

Note that, in this configuration, it is favorable that the lenses 153 of the plug-side connector 15 are not collimate lenses but condenser lenses that collect emitted light onto the photodiodes 192.

Also with the configuration as described above, it is possible to separate the plug-side connector 15 from the receptor-side connector 19 and subject the image pickup unit 11 to sterilization treatment. Since the main body unit 12 does not need to be subjected to sterilization treatment, it can also have a configuration not having a high environment resistance.

Note that the plug-side connector 15 and the receptor-side connector 18 according to this embodiment are not limited to be applied to the endoscope system and can be applied to various medical instruments using optical communication, which are required to have a high environment resistance.

Second Embodiment

An endoscope system according to a second embodiment of the present technology will be described.

[Configuration of Endoscope System]

Figure 14:
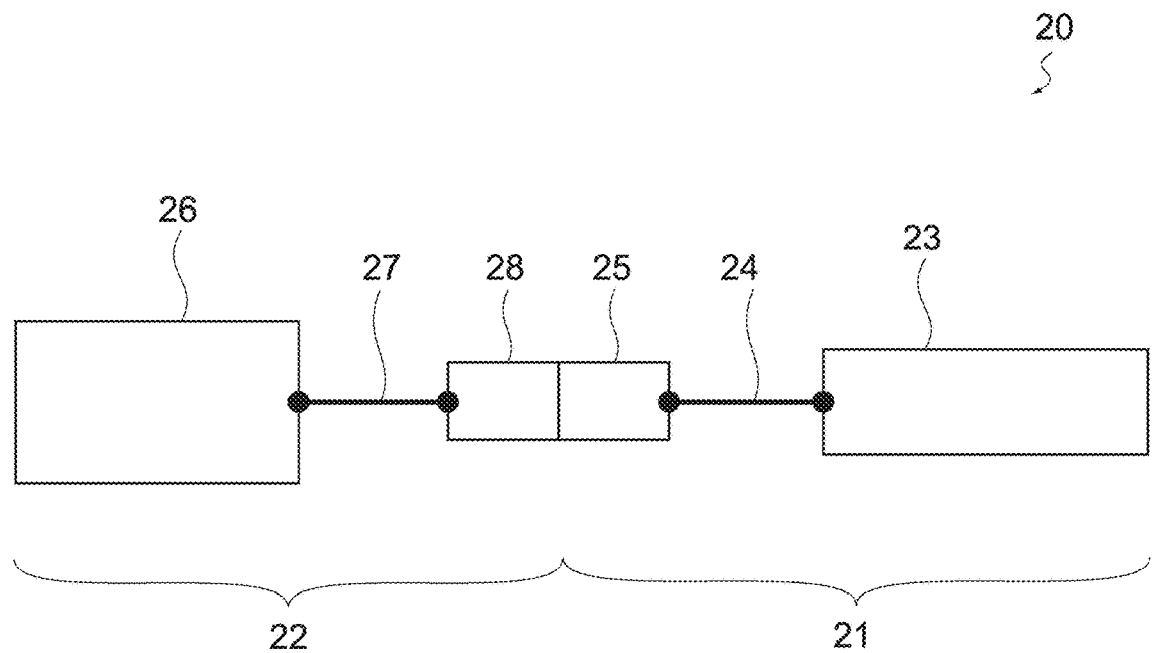
FIG. 14 A schematic view of an endoscope system according to a second embodiment of the present technology.

FIG. 14 is a schematic view showing a configuration of an endoscope system 20 according to this embodiment. As shown in the figure, the endoscope system 10 is constituted of an image pickup unit 21 and a main body unit 22.

The image pickup unit 21 includes an image pickup distal end 23, a cable 24, and a plug-side connector 25. Configurations of the image pickup distal end 23 and the cable 24 are identical to the configurations of the image pickup distal end 13 and the cable 14 according to the first embodiment, and hence descriptions thereof will be omitted. The plug-side connector 25 is detachably connected to a receptor-side connector 28 to be described later and sends optical signals to the receptor-side connector 28. The plug-side connector 25 will be described later in detail. Once the connection of the plug-side connector 25 and the receptor-side connector 28 is cancelled, the image pickup unit 21 can be detached from the main body unit 22.

The main body unit 22 includes a main body 26, a cable 27, and the receptor-side connector 28. Configurations of the main body 26 and the cable 27 are identical to the configurations of the main body 16 and the cable 17 according to the first embodiment, and hence descriptions thereof will be omitted. The receptor-side connector 28 is detachably connected to the plug-side connector 25 and receives optical signals from the plug-side connector 25. The receptor-side connector 28 will be described later in detail.

The main body unit 22 has the configuration as described above. Note that the main body unit 22 does not necessarily need to include the cable 27 and the main body 26 may be directly provided with the receptor-side connector 28. In this case, the receptor-side connector 28 and the photoelectric conversion device can be connected to each other through optical fibers arranged within the main body 26.

[Structure of Optical Connector]

Figure 15:
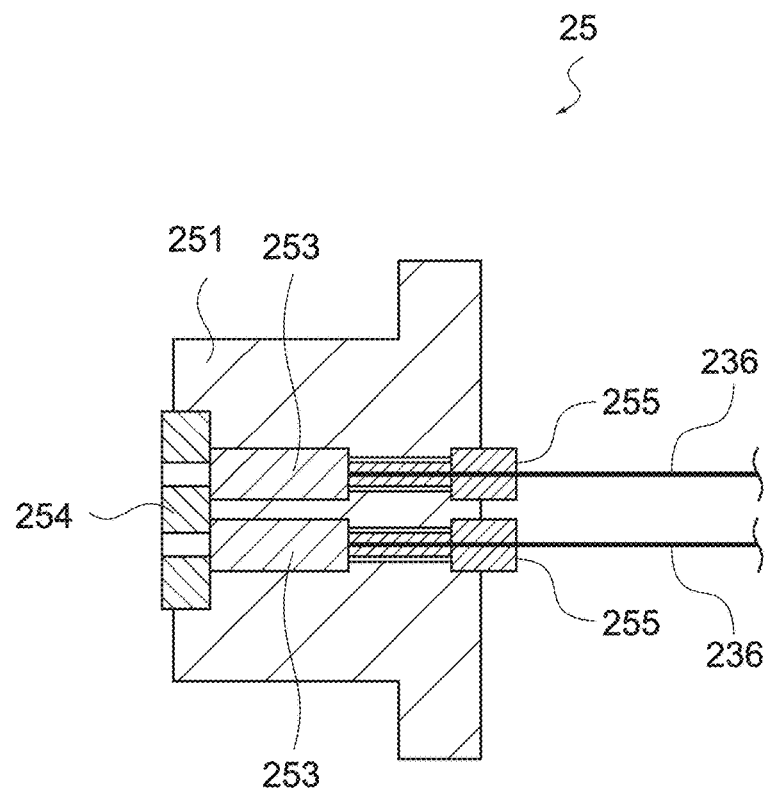
FIG. 15 A cross-sectional view of a plug-side connector of the endoscope system.
Figure 16:
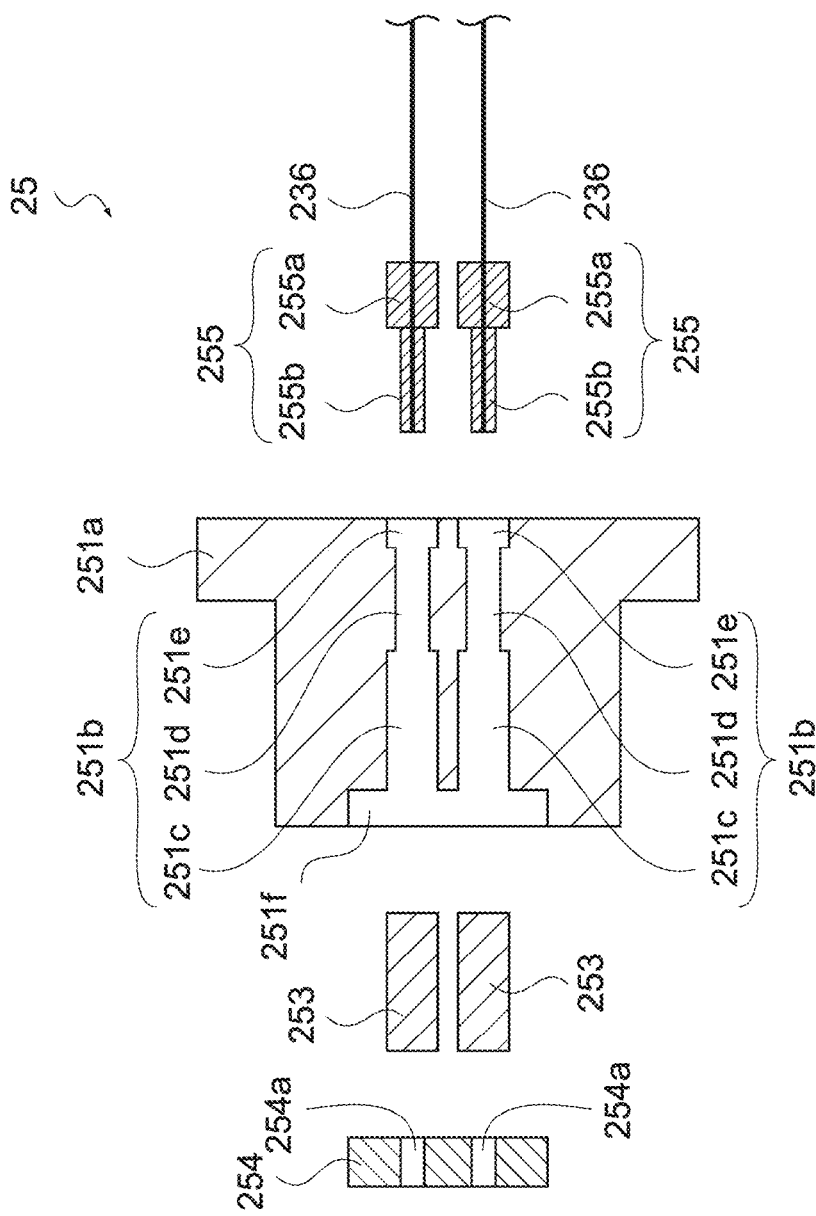
FIG. 16 An exploded view of the plug-side connector of the endoscope system.
Figure 17:
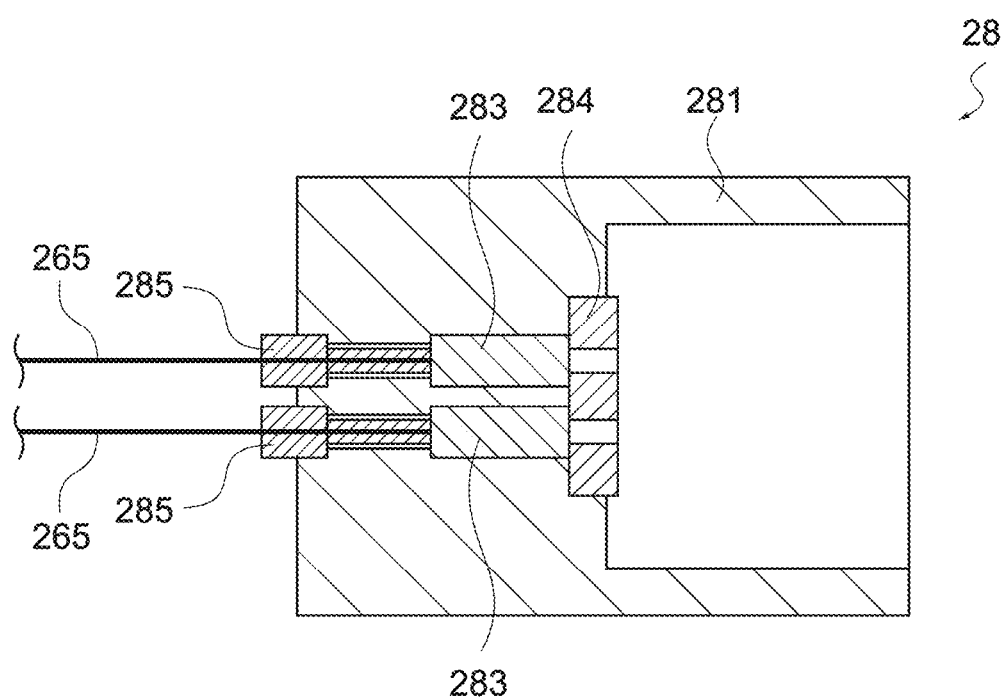
FIG. 17 A cross-sectional view of a receptor-side connector of the endoscope system.
Figure 18:
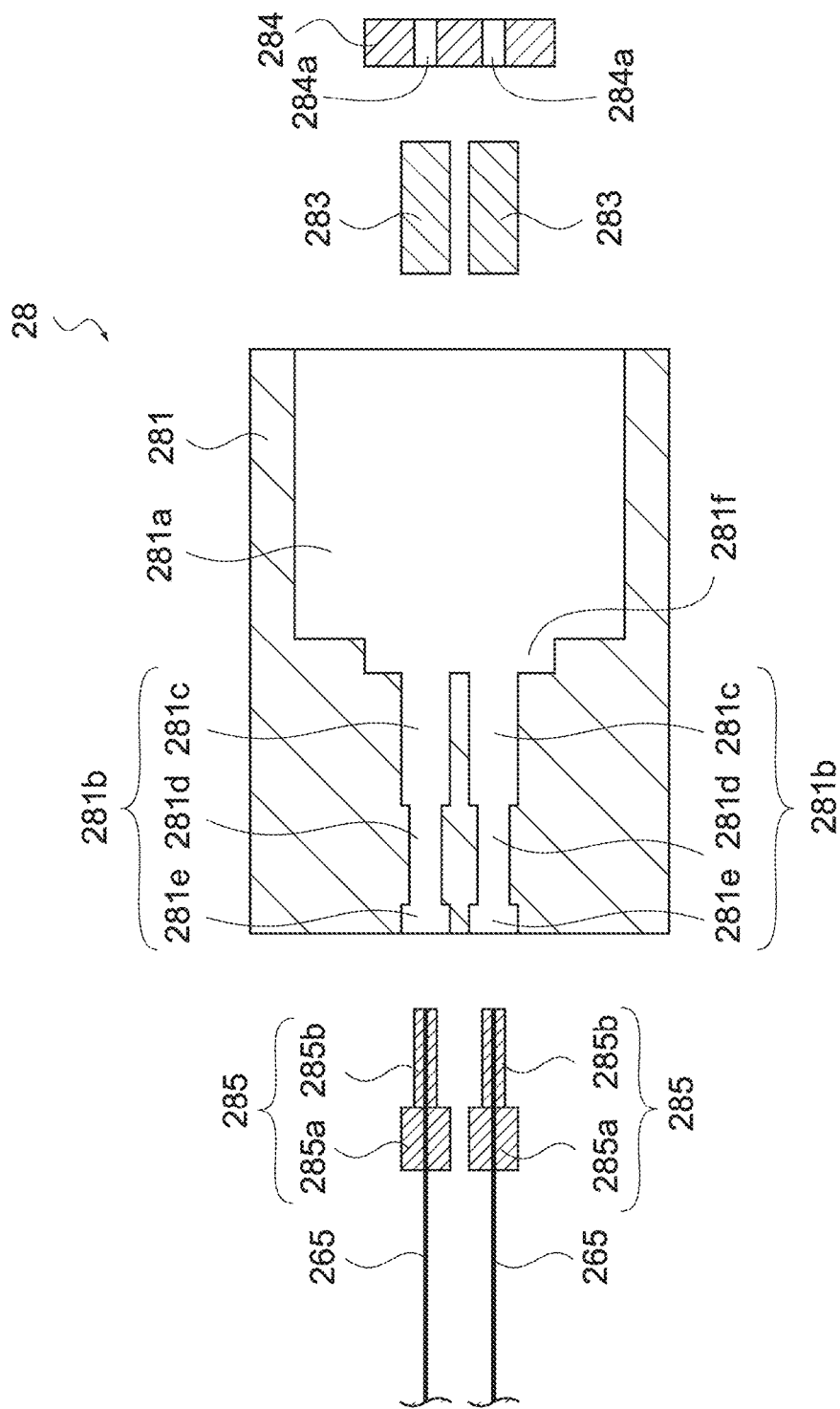
FIG. 18 An exploded view of the receptor-side connector of the endoscope system.
Figure 19:
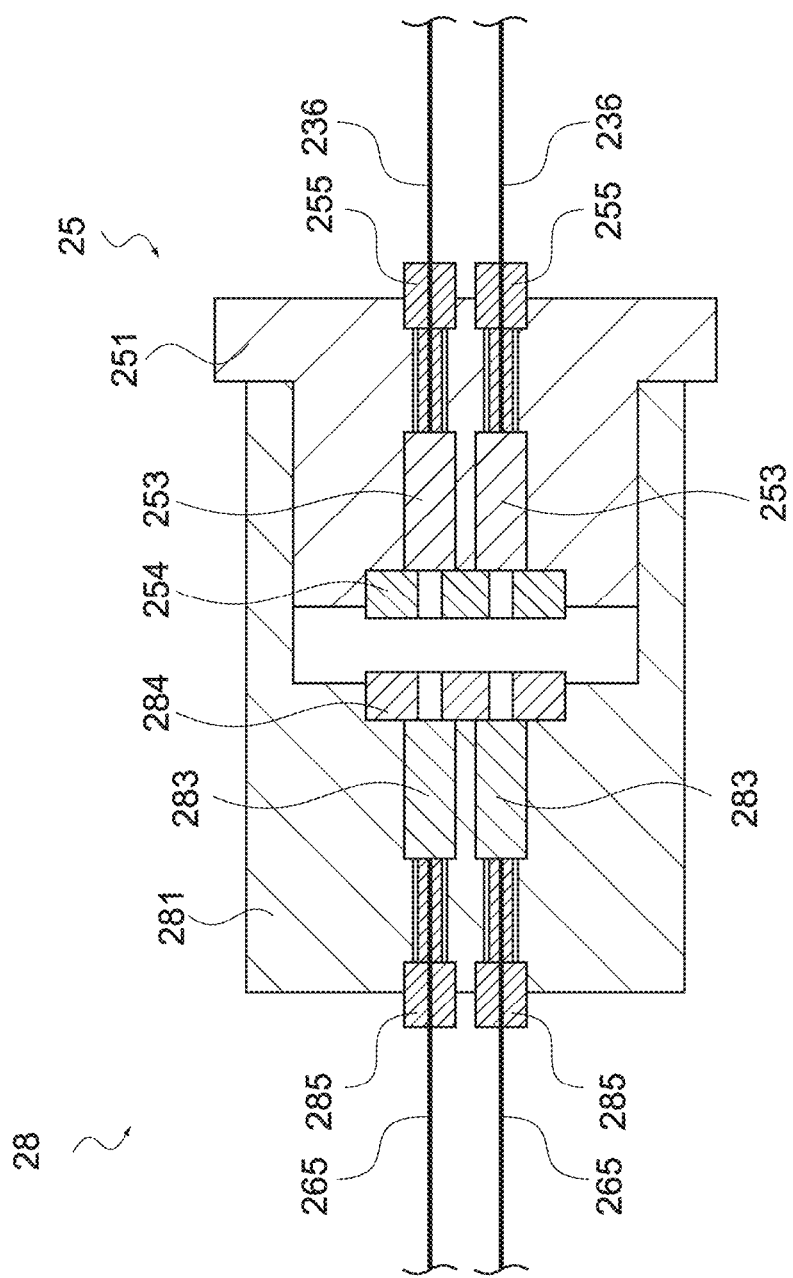
FIG. 19 A cross-sectional view showing a state of connection between the plug-side connector and the receptor-side connector of the endoscope system.

The plug-side connector 25 and the receptor-side connector 28 according to this embodiment will be described. FIG. 15 is a cross-sectional view of the plug-side connector 25. FIG. 16 is an exploded view of the plug-side connector 25. FIG. 17 is a cross-sectional view of the receptor-side connector 28. FIG. 18 is an exploded view of the receptor-side connector 28. FIG. 19 is a cross-sectional view showing a state in which the plug-side connector 25 and the receptor-side connector 28 are connected to each other.

As shown in FIGS. 15 and 16, the plug-side connector 25 is constituted of a connector frame 251, lenses 253, a lens retainer 254, fiber ferrules 255, and optical fibers 236.

Figure 20:
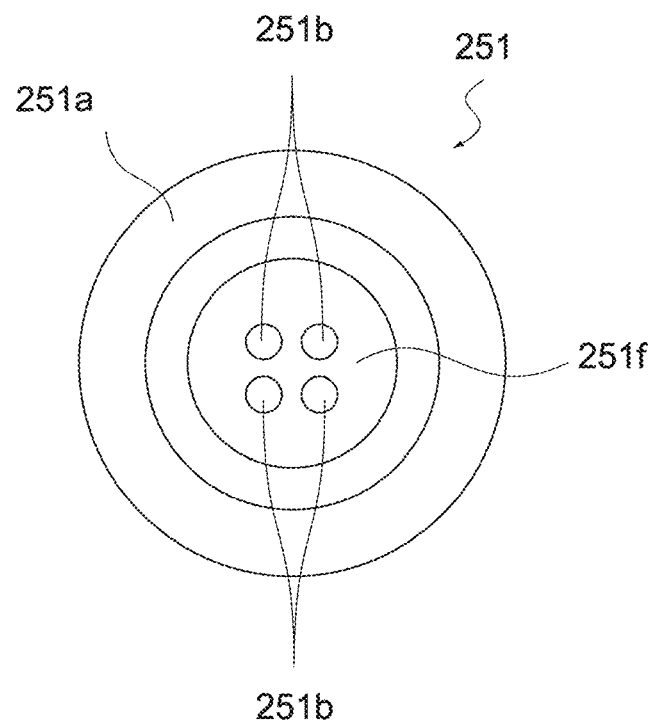
FIG. 20 A plan view of a connector frame of the plug-side connector of the endoscope system.

The connector frame 251 is a member fitted in connector frame 281 of the receptor-side connector 28 as shown in FIG. 19. FIG. 20 is a plan view of the connector frame 251 and is a view as the connector frame 251 is viewed in the direction of the distal end (direction opposite to the optical fibers 236).

As shown in FIGS. 16 and 20, the connector frame 251 has a columnar shape and a projection 251a is provided in an outer circumferential surface thereof. When the connector frame 251 is fitted in the connector frame 281, the projection 251a comes into contact with the connector frame 281 and defines the position of the plug-side connector 25 with respect to the receptor-side connector 28. Note that the connector frame 251 is not limited to the columnar shape and only needs to have a shape that can be fitted in the connector frame 281.

Further, the connector frame 251 include through-holes 251b. The number of through-holes 251b is identical to the number of optical fibers 236 connected to the plug-side connector 25. Hereinafter, although descriptions will be made assuming that the number of optical fibers 236 is 4, it does not need to be 4 and the number of through-holes 251b can also be appropriately changed in a manner that depends on the number of optical fibers 236.

As shown in FIG. 16, the through-hole 251b is constituted of a first hole portion 251c, a second hole portion 251d, and a third hole portion 251e. The second hole portion 251d is a portion having a smaller diameter than that of each of the first hole portion 251c and the third hole portion 251e. Each of the first hole portion 251c and the third hole portion 251e can have a diameter of, for example, 2.04 mm. Note that the diameter of the first hole portion 251c and the diameter of the third hole portion 251e do not need to be the same.

Further, the connector frame 251 includes a recess portion 251f. As shown in FIGS. 16 and 20, the recess portion 251f is formed continuously with the first hole portions 251c. The recess portion 251f can have a disk-like, recess-like shape, though not limited thereto.

Although the material of the connector frame 251 is not particularly limited, a material excellent in the environment resistance and having elasticity suitable for fitting in the connector frame 281 is favorable. Specifically, the connector frame 251 can be made of stainless steel, aluminum, or zirconia. Further, the connector frame 251 may be made of a plated metal material, for example, may be made of a brass base material plated with Ni.

The lenses 253, the lens retainer 254, the fiber ferrules 255, and the optical fibers 236 have configurations similar to those in the first embodiment.

The lenses 253 are inserted into the first hole portions 251c of the through-holes 251b and convert optical paths of light output from the optical fibers 236. Specifically, the lenses 253 are collimate lenses and can enlarge and collimate light emitted from the optical fibers 236. The lenses 253 can each have a columnar shape, for example, and a diameter of, for example, 2.00 mm.

One lens 253 can be arranged for each through-hole 251b, that is, a total of four lenses 253 can be arranged. However, a number of lenses 253 depending on the number of optical fibers 236 (number of through-holes 251b) connected to the plug-side connector 25 can be arranged. Each lens 253 is sandwiched and positioned by the lens retainer 254 the fiber ferrules 255. Although the material of the lenses 253 is not particularly limited, a material excellent in the environment resistance, such as glass, is favorable.

The lens retainer 254 is press-fitted in the recess portion 251f of the connector frame 251 and positions the lenses 253. As shown in FIG. 16, the lens retainer 254 includes openings 254a. The openings 254a are arranged facing the respective lenses 253 and an identical number of openings 254a to the number of lenses 253 are provided. The opening 254a has a diameter smaller than a diameter of the lens 253 and is formed in such a manner that the entire opening 254a faces the lens 253. The opening 254a can have a diameter of, for example, 1.60 mm.

The lens retainer 254 can have the disk-like shape, though not limited thereto. The lens retainer 254 only needs to have a shape conforming to the recess portion 251f. Although the material of the lens retainer 254 is not particularly limited, a material excellent in the environment resistance is favorable. Further, the openings 254a are formed in the lens retainer 254, and hence the lens retainer 254 can be made of a material not having light transmissivity. Specifically, the lens retainer 254 can be made of stainless steel, aluminum, or zirconia. Further, the lens retainer 254 may be made of a plated metal material, for example, may be made of a brass base material plated with Ni.

The fiber ferrules 255, to which the optical fibers 236 are connected, are press-fitted in the through-holes 251b. One fiber ferrule 255 is arranged for each optical fiber 236. As shown in FIG. 16, the fiber ferrule 155 includes a base portion 255a and a smaller-diameter portion 255b.

The optical fibers 236 are inserted from the base portions 255a to ends of the smaller-diameter portions 255b. As shown in FIGS. 15 and 16, the base portions 255a are press-fitted in the third hole portion 251e. The smaller-diameter portions 255b may be held in contact with inner circumferential surfaces of the second hole portions 251d or may be separated from the inner circumferential surfaces. By the fiber ferrules 255 being press-fitted in the through-holes 251b, the lenses 253 are sandwiched by the fiber ferrules 255 and the lens retainer 254 and the optical fibers 236 are held in contact with the lenses 253.

A material excellent in the environment resistance of the fiber ferrules 255 is favorable. For example, the base portion 255a can be made of stainless steel and the smaller-diameter portion 255b can be made of zirconia. The base portion 255a and the smaller-diameter portion 255b may be made of identical materials.

The optical fibers 236 are fixed to a lens holder 252 through the fiber ferrules 255 and transfer optical signals output by the photoelectric conversion device to the lenses 253. The number of optical fibers 236 is not limited to four as described above and may be three or less or five or more. Although the optical fiber 236 can have a general structure made of a glass, a synthetic resin, or the like, one excellent in the environment resistance is favorable.

The plug-side connector 25 has the structure as described above. Note that the structure of the plug-side connector 25 is not limited to the above-mentioned one. For example, the plug-side connector 25 may be made of a light-transmissive material as in the plug-side connector 15 according to the first embodiment and include a cover member that covers the lens retainer 254.

As shown in FIGS. 17 and 18, the receptor-side connector 28 is constituted of the connector frame 281, lenses 283, a lens retainer 284, fiber ferrules 285, and optical fibers 265.

Figure 21:
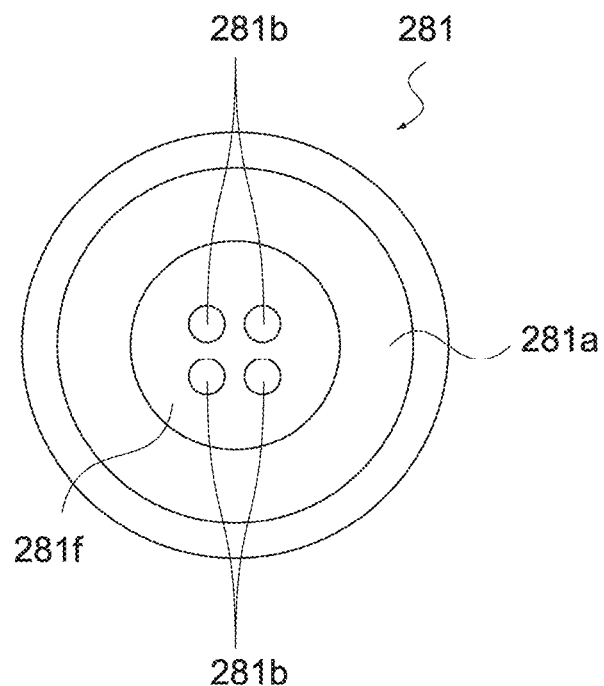
FIG. 21 A plan view of a connector frame of the receptor-side connector of the endoscope system.

The connector frame 281 is a member fitted on the connector frame 251 of the plug-side connector 25 as shown in FIG. 19. FIG. 21 is a plan view of the connector frame 281 and is a view as the connector frame 281 is viewed in the direction of the distal end (direction opposite to the optical fibers 265).

As shown in FIGS. 17 and 21, the connector frame 281 includes a recess portion 281a. When the connector frame 281 is fitted on the connector frame 251, an inner circumferential surface of the recess portion 281a is held in contact with an outer circumferential surface of the connector frame 251. The recess portion 281a can have a diameter of, for example, 8 mm.

Further, the connector frame 281 includes through-holes 281b. The number of through-holes 281b is identical to the number of optical fibers 265 connected to the receptor-side connector 28 and can be appropriately changed in a manner that depends on the number of optical fibers 265. The through-hole 281b is constituted of a first hole portion 281c, a second hole portion 281d, and a third hole portion 281e. The second hole portion 281d is a portion having a smaller diameter than that of each of the first hole portion 281c and the third hole portion 281e. Each of the first hole portion 281c and the third hole portion 281e can have a diameter of, for example, 2.04 mm. Note that the diameter of the first hole portion 281c and the diameter of the third hole portion 281e do not need to be the same.

In addition, the connector frame 281 includes a recess portion 281f. As shown in FIG. 18, the recess portion 281f is formed continuously with the first hole portions 281c. The recess portion 281f can have a disk-like, recess-like shape, though not limited thereto.

Although the material of the connector frame 281 is not particularly limited, a material excellent in the environment resistance and having elasticity suitable for fitting on the connector frame 251 is favorable. Specifically, the connector frame 281 can be made of stainless steel, aluminum, or zirconia. Further, the connector frame 281 may be made of a plated metal material, for example, may be made of a brass base material plated with Ni.

Configurations of the lenses 283, the lens retainer 284, and the fiber ferrules 285 can be identical to the configurations in the plug-side connector 25.

The lenses 283 are inserted into the first hole portions 281c of the through-holes 281b and convert optical paths of the entering light. Specifically, the lenses 283 are collimate lenses and can collect light entering from the lenses 253 of the plug-side connector 25 and cause it to enter the optical fibers 265.

One lens 283 can be arranged for each through-hole 281b, that is, a total of four lenses 283 can be arranged. However, a number of lenses 283 depending on the number of optical fibers 265 (number of through-holes 281b) connected to the receptor-side connector 28 can be arranged. Each lens 283 is sandwiched and positioned by the lens retainer 284 and the fiber ferrules 285. Although the material of the lenses 283 is not particularly limited, a material excellent in the environment resistance, such as glass, is favorable. The lenses 283 can each have a columnar shape, for example, and a diameter of, for example, 2.00 mm.

The lens retainer 284 is press-fitted in the recess portion 281f of the connector frame 281 and positions the lenses 283. As shown in FIG. 18, the lens retainer 284 includes openings 284a. The openings 284a are arranged facing the respective lenses 283 and an identical number of openings 284a to the number of lenses 283 are provided. The opening 284a has a diameter smaller than a diameter of the lens 283 and is formed in such a manner that the entire opening 284a faces the lens 283. The opening 284a can have a diameter of, for example, 1.60 mm.

The lens retainer 284 can have the disk-like shape, though not limited thereto. The lens retainer 284 only needs to have a shape conforming to the recess portion 281f. Although the material of the lens retainer 284 is not particularly limited, a material excellent in the environment resistance is favorable. Further, the openings 284a are formed in the lens retainer 284, and hence the lens retainer 284 can be made of a material not having light transmissivity. Specifically, the lens retainer 284 can be made of stainless steel, aluminum, or zirconia. Further, the lens retainer 284 may be made of a plated metal material, for example, may be made of a brass base material plated with Ni.

The fiber ferrules 285, to which the optical fibers 265 are connected, are press-fitted in the through-holes 281b. One fiber ferrule 285 is arranged for each optical fiber 265. As shown in FIG. 18, the fiber ferrule 285 includes a base portion 285a and a smaller-diameter portion 285b.

The optical fibers 265 are inserted from the base portions 285a to ends of the smaller-diameter portions 285b. As shown in FIGS. 17 and 18, the base portions 285a are press-fitted in the third hole portions 281e. The smaller-diameter portions 285b may be held in contact with inner circumferential surfaces of the second hole portions 282e or may be separated from the inner circumferential surfaces. By the fiber ferrules 285 being press-fitted in the through-holes 281b, the lenses 283 are sandwiched by the fiber ferrules 285 and the lens retainer 284 and the optical fibers 265 are held in contact with the lenses 283.

A material excellent in the environment resistance of the fiber ferrules 285 is favorable. For example, the base portion 285a can be made of stainless steel and the smaller-diameter portion 285b can be made of zirconia. The base portion 285a and the smaller-diameter portion 285b may be made of identical materials.

The optical fibers 265 are fixed to a lens holder 282 through the fiber ferrules 285 and transfer optical signals transferred from the plug-side connector 25 to the photoelectric conversion device. The number of optical fibers 265 is not limited to four as described above and may be three or less or five or more. Although the optical fiber 265 can have a general structure made of a glass, a synthetic resin, or the like, one excellent in the environment resistance is favorable.

The receptor-side connector 28 has the structure as described above. Note that the structure of the receptor-side connector 28 is not limited to the above-mentioned one. For example, the receptor-side connector 28 may be made of a light-transmissive material as in the receptor-side connector 18 according to the first embodiment and include a cover member that covers the lens retainer 284.

[Operation of Endoscope System]

The endoscope system according to this embodiment operates in a way similar to that of the endoscope system 10 according to the first embodiment. That is, optical signals output from the image pickup distal end are emitted from the optical fibers 236 and enter the lenses 253 in the plug-side connector 25 (see FIG. 19). The lenses 253 enlarge and collimate light (optical signals) emitted from the optical fibers 236. The light emitted from the lenses 253 passes through the openings 254a (see FIG. 16) provided in the lens retainer 254 and is emitted to the receptor-side connector 28.

The light entering the receptor-side connector 28 passes through the openings 284a (see FIG. 18) provided in the lens retainer 284 and enters the lenses 283. The light entering the lenses 283 is collected by the lenses 283, enters the optical fibers 265, and is transferred to the main body 26.

The plug-side connector 25 and the receptor-side connector 28 are provided with the lenses (lenses 253 and lenses 283) and the diameter of the optical path of light transferred between the both connectors is enlarged. Therefore, high precision is not required for positioning the plug-side connector 25 and the receptor-side connector 28.

[Effects of Endoscope System]

As in the first embodiment, the respective members in the plug-side connector 25 and the receptor-side connector 28 are joined to each other by press-fitting, and hence the use of adhesives is unnecessary. Therefore, the plug-side connector 25 and the receptor-side connector 28 have a high environment resistance (thermal resistance, humidity resistance, pressure resistance, etc.).

Further, the number of components of the plug-side connector 25 and the receptor-side connector 28 in this embodiment is smaller than the number of components of the plug-side connector 15 and the receptor-side connector 18 according to the first embodiment. Thus, assembly simplification and improvements in positional errors due to component tolerance and the like become possible. On the other hand, the shapes of the connector frame 251 and the connector frame 281 are more complicated than those of the connector frame 151 and the connector frame 181 according to the first embodiment. Thus, a high workability is necessary.

Modified Examples

The configuration of the endoscope system 20 is not limited to the above-mentioned one. For example, the plug-side connector 25 and the receptor-side connector 28 can also be provided with wires for electrical signals such that the plug-side connector 25 and the receptor-side connector 28 are configured to be capable of transferring electrical signals in addition to optical signals. The wires for electrical signals can be provided inside the connector frames or inside the lens holders of the both connectors. Further, the endoscope system 20 may include a connector for electrical signals other than the plug-side connector 25 and the receptor-side connector 28.

Further, the coupling mechanism of the plug-side connector 25 and the receptor-side connector 28 is also not limited to the above-mentioned configuration. In the above-mentioned configuration, the configuration in which the connector frame 251 inserted into the connector frame 281 has been employed. However, conversely, to be specific, the connector frame 281 may be inserted into the connector frame 251.

In addition, in order to make transfer positions of optical signals between the both connectors (positions of the openings 254a and the openings 284a) correspond to each other, the shape of the connector frame 251 and the shape of the connector frame 281 may be replaced by a shape which is not a rotationally-symmetric shape (rectangular shape or polygonal shape as viewed in the direction of the distal end). The connector frame 251 and the connector frame 281 can also be provided with lock mechanisms for mutually fixing their positions.

Further, the endoscope system 20 only needs to include at least one connector having the above-mentioned configuration and either one of the plug-side connector 25 and the receptor-side connector 28 does not need to have the above-mentioned configuration. For example, as in the first embodiment, the receptor-side connector may include photodiodes. In this case, it is favorable that the lenses 253 of the plug-side connector 25 are not collimate lenses but condenser lenses that collect emitted light onto the photodiodes.

Note that the plug-side connector 25 and the receptor-side connector 28 according to this embodiment is not limited to the endoscope system and can be applied to various medical instruments using optical communication, which are required to have a high environment resistance.

Third Embodiment

An endoscope system according to a third embodiment of the present technology will be described.

[Configuration of Endoscope System]

Figure 22:
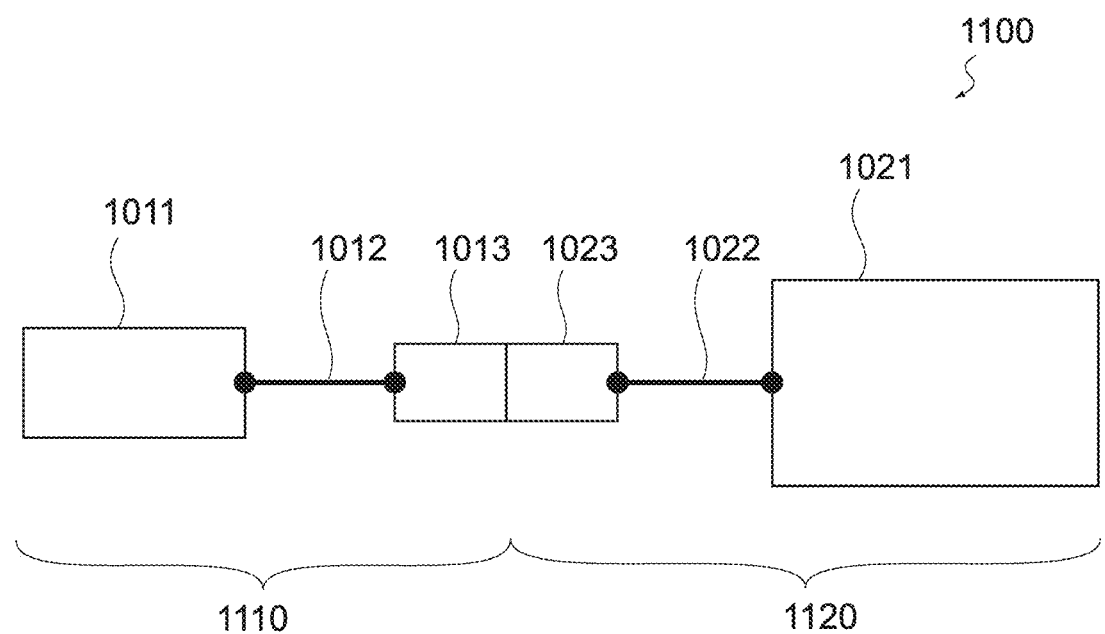
FIG. 22 A schematic view an endoscope system according to a third embodiment of the present technology.

FIG. 22 is a schematic view showing a configuration of an endoscope system 1100 according to this embodiment. As shown in the figure, the endoscope system 1100 is constituted of an endoscope 1110 and a signal processing apparatus 1120.

The endoscope 1110 includes an insertion portion 1011, a cable 1012, and a connector 1013. As will be described later, regarding a configuration of the endoscope 1110, an image picked up at the insertion portion 1011 is converted into optical signals at the insertion portion 1011 and transferred to the connector 1013 via the cable 1012.

The signal processing apparatus 1120 includes a main body 1021, a cable 1022, and a connector 1023. The connector 1023 is attachable/detachable from the connector 1013. The above-mentioned optical signals are transferred to connector 1023 from the connector 1013. The optical signals are transferred to the main body 1021 through the cable 1022. The main body 1021 includes at least a photoelectric conversion device and converts the transferred optical signals into electrical signals.

Connected to the signal processing apparatus 1120, the endoscope 1110 is used for a surgical operation. Images picked up at the insertion portion 1011 are transferred to the signal processing apparatus 1120. After the surgical operation, the connection of the connector 1013 with the connector 1023 is cancelled and the endoscope 1110 is detached form the signal processing apparatus 1120 and subjected to sterilization treatment with an autoclave or the like.

[Configuration of Endoscope]

Figure 23:
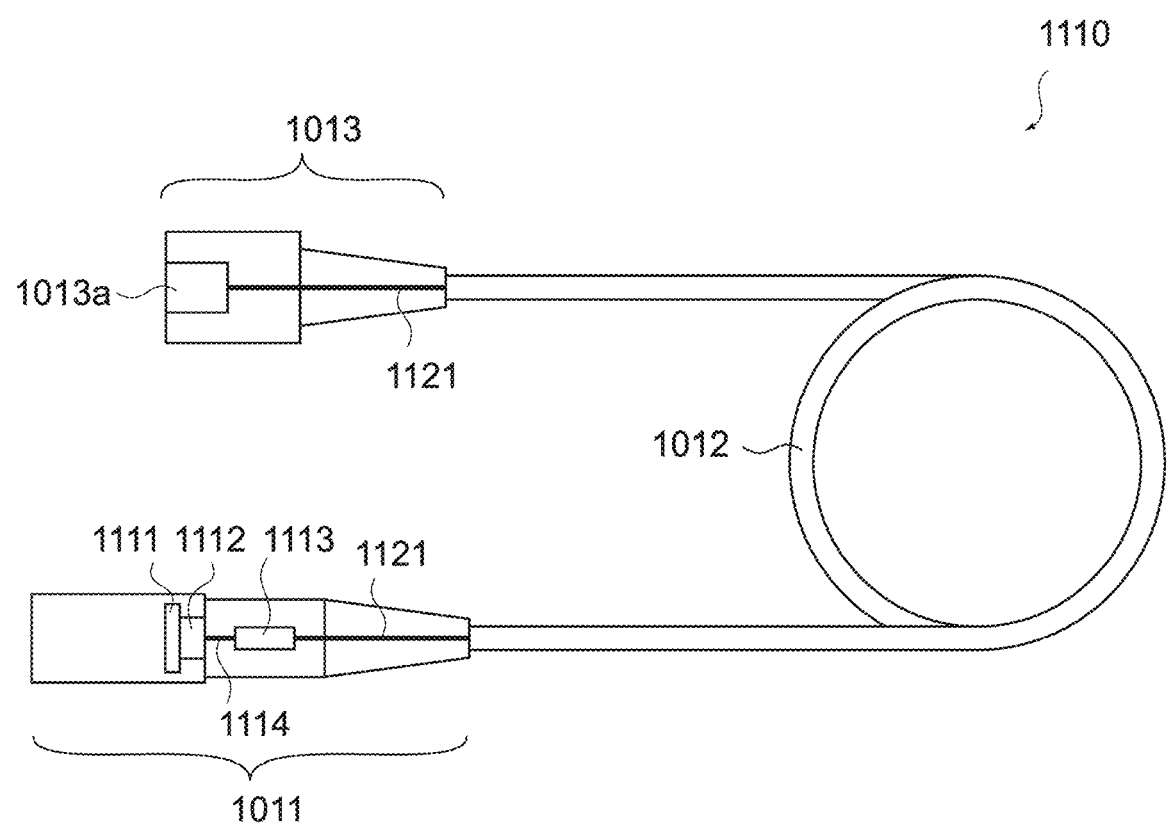
FIG. 23 A schematic view of an endoscope of the endoscope system.

FIG. 23 is a schematic view of the endoscope 1110 according to this embodiment. As shown in the figure, the endoscope 1110 includes an insertion portion 1011, a cable 1012, and a connector 1013.

The insertion portion 1011 is a portion inserted into a body cavity of the patient and includes an image pickup device 1111, an electrical signal processing unit 1112, and an optical transmission module 1113. The image pickup device 1111 and the electrical signal processing unit 1112 are connected to the optical transmission module 1113 through an electrical signal line 1114 and the optical transmission module 1113 is connected to an optical fiber 1121.

The image pickup device 1111 is a CCD (Charge Coupled Device) image sensor or a CMOS (Complementary Metal Oxide Semiconductor) image sensor and picks up an image via an image pickup optical system (not shown) and generates electrical signals of the image. The image pickup device 1111 outputs the generated electrical signals to the electrical signal processing unit 1112.

The electrical signal processing unit 1112 subjects the electrical signals supplied from the image pickup device 1111 to signal processing for transmission and outputs them to the optical transmission module 1113 via the electrical signal line 1114.

The optical transmission module 1113 converts the electrical signals supplied from the electrical signal processing unit 1112 into optical signals and outputs them to the optical fiber 1121. A configuration of the optical transmission module 1113 will be described later.

The cable 1012 connects the insertion portion 1011 and the connector 1013 to each other. The cable 1012 includes the optical fiber 1121 and transfers optical signals from the insertion portion 1011 to the connector 1013. Further, the cable 1012 may include a wire for electrical signals in addition to the optical fiber 1121.

The connector 1013 is detachably connected to the connector 1023 of the signal processing apparatus 1120 and transfers optical signals supplied from the optical fiber 1121 to the signal processing apparatus 1120. The connector 1013 can include a recess portion 1013a and be connected to the signal processing apparatus 1120 by the connector 1023 being inserted into the recess portion 1013a. The connector 1013 may be a photoelectric composite connector that exchanges electrical signals between the connector 1013 and the signal processing apparatus 1120 in addition to the optical signals.

[Configuration of Optical Transmission Module]

Figure 24:
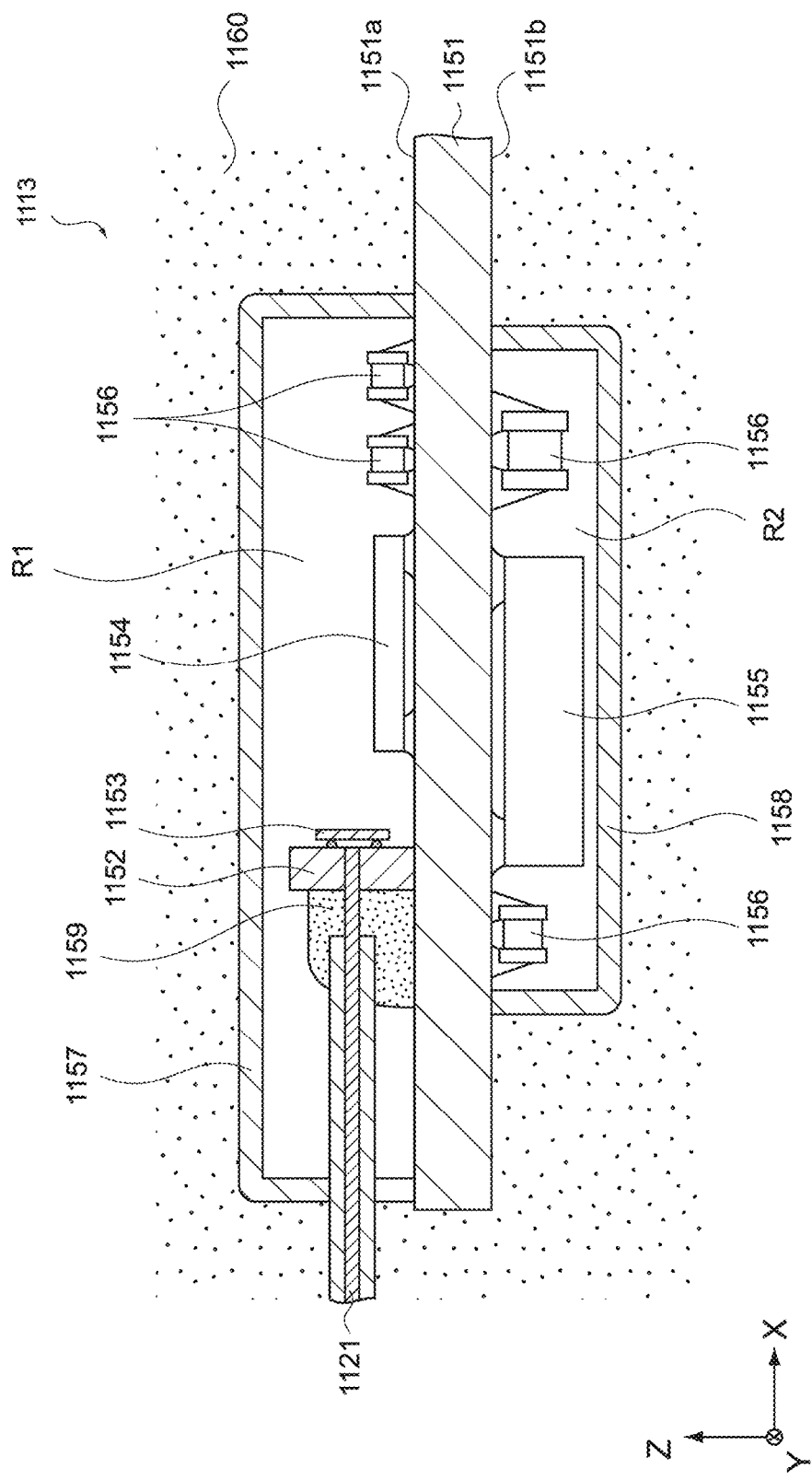
FIG. 24 A schematic view of an optical transmission module of the endoscope.

FIG. 24 is a schematic view showing a configuration of the optical transmission module 1113. As shown in the figure, the optical transmission module 1113 includes a first substrate 1151, a second substrate 1152, a light-emitting device 1153, an IC (Integrated Circuit) 1154 for driving the light-emitting device, an IC for control 1155, passive devices 1156, a first shield case 1157, a second shield case 1158, an adhesive resin 1159, and a sealing resin 1160. Note that three directions orthogonal to one another in the figures below are shown as an X-direction, a Y-direction, and a Z-direction.

The first substrate 1151 supports the respective components and electrically connects them to one another. An organic multi-layer substrate, a multi-layer ceramic substrate, or the like, which is made of silicon, quartz, glass, ceramics, or an organic material, can be used for the first substrate 1151. Hereinafter, one surface of the first substrate 1151 will be referred to as a first surface 1151a and a surface opposite thereto will be referred to as a second surface 1151b.

Figure 25:
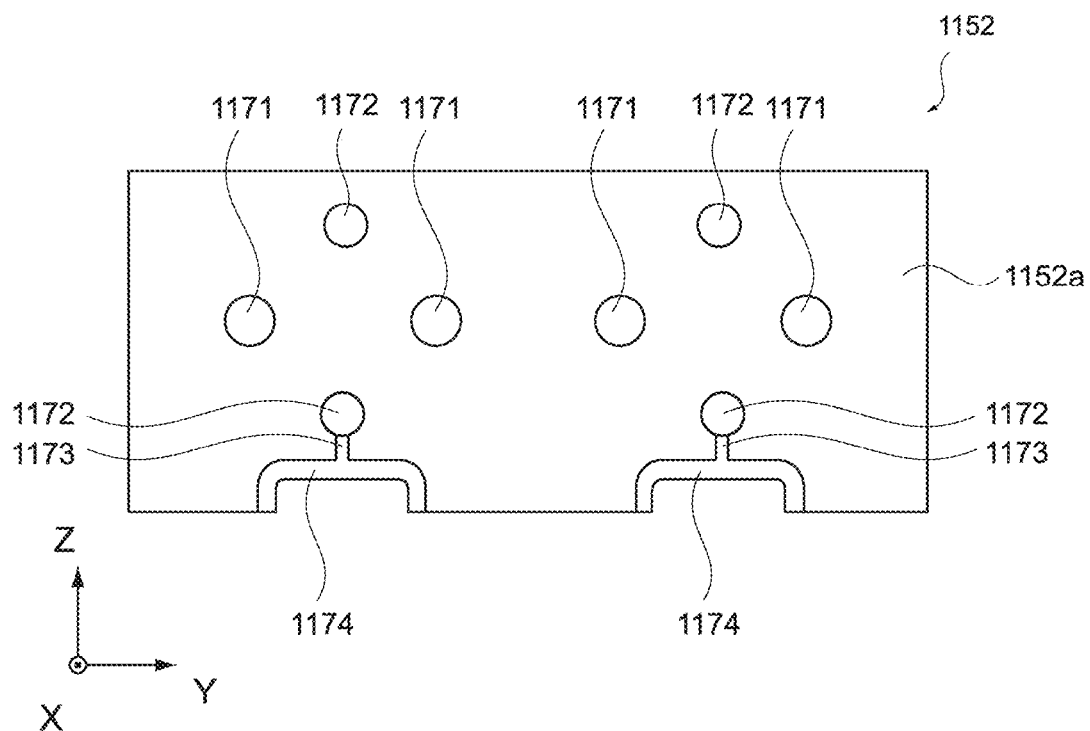
FIG. 25 A plan view of a second substrate of the optical transmission module.
Figure 26:
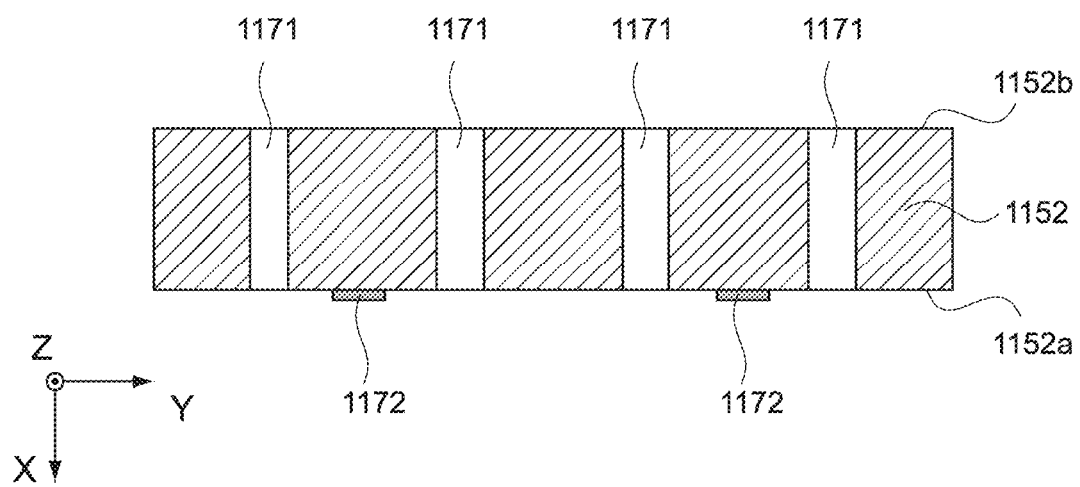
FIG. 26 A cross-sectional view of the second substrate of the optical transmission module.
Figure 27:
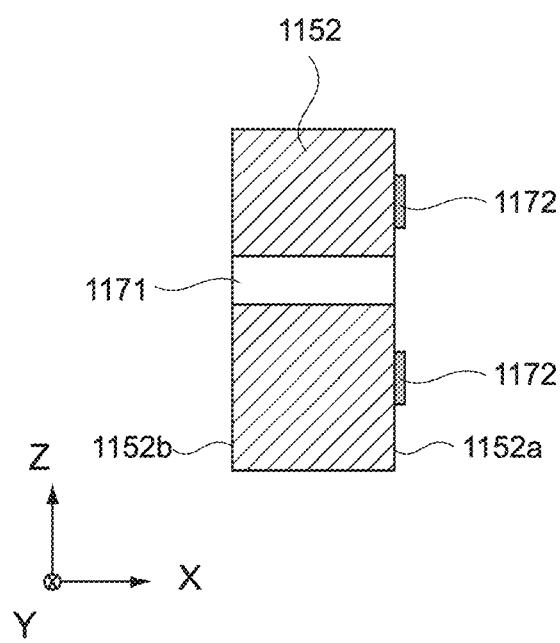
FIG. 27 A cross-sectional view of the second substrate of the optical transmission module.

The second substrate 1152 is electrically connected to the first surface 1151a. The optical fiber 1121 and the light-emitting device 1153 are connected to the second substrate 1152. FIG. 25 is a plan view of the second substrate 1152. FIGS. 26 and 27 are cross-sectional views of the second substrate 1152. FIG. 26 is a cross-sectional view in the X-Y plane. FIG. 27 is a cross-sectional view taken along the Z-X plane.

The second substrate 1152 can be made of silicon, quartz, glass, ceramics, or an organic material. At least the surface of the second substrate 1152 can be insulative. If the second substrate 1152 is made of an electrically conductive material, an insulating layer such as an oxide film can be formed on the surface. Hereinafter, one surface of the second substrate 1152 will be referred to as a first surface 1152a and a surface opposite thereto will be referred to as a second surface 1152b.

As shown in FIGS. 25 to 27, the second substrate 1152 includes through-holes 1171, electrodes 1172 for the light-emitting device, wires 1173, and terminals 1174.

Figure 28:
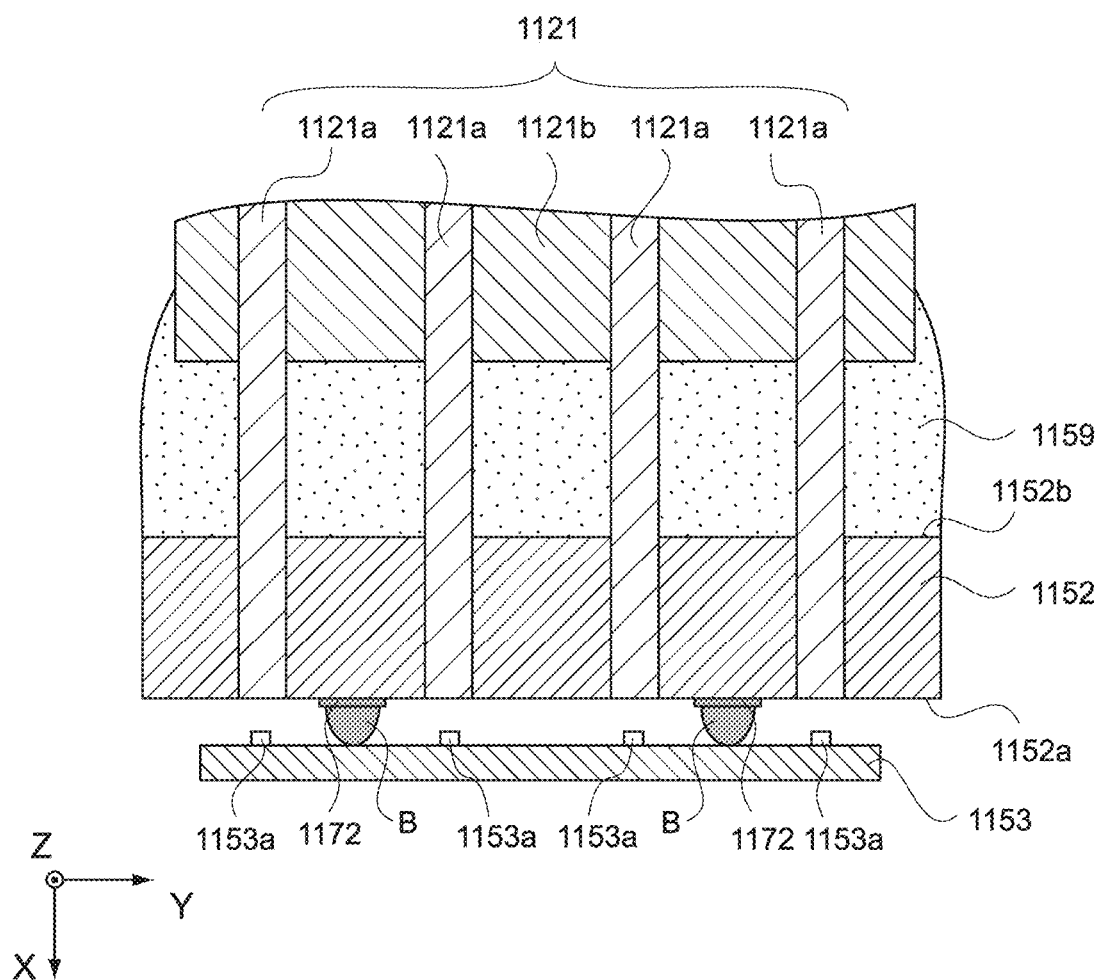
FIG. 28 A cross-sectional view showing connection of the second substrate of the optical transmission module, an optical fiber, and a light-emitting device.
Figure 29:
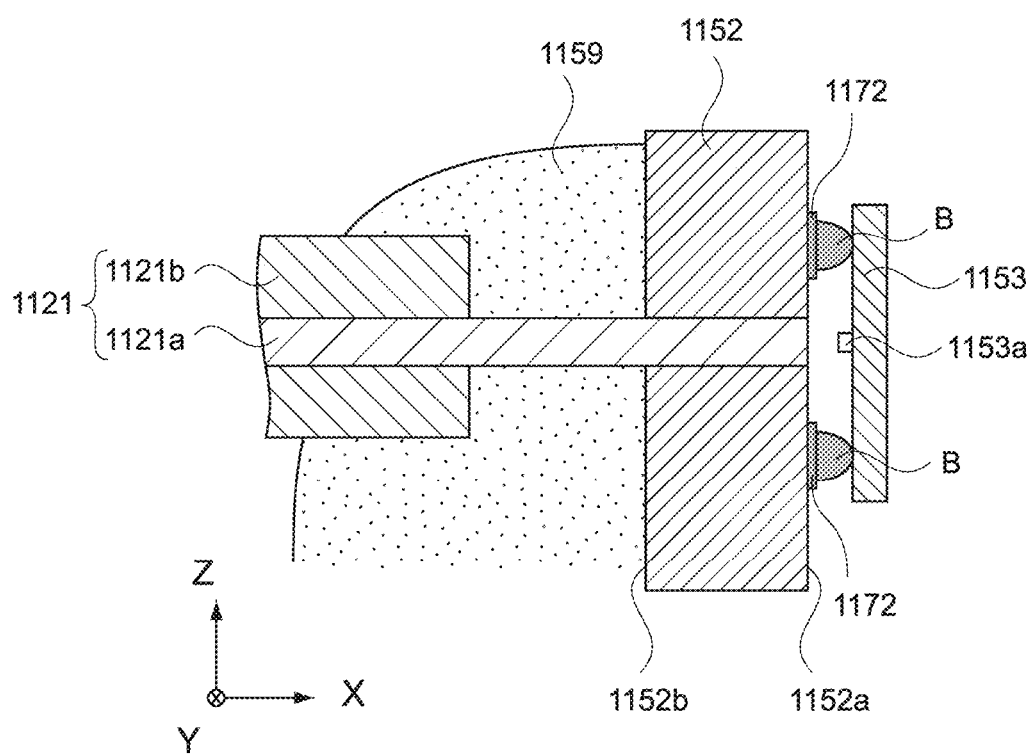
FIG. 29 A cross-sectional view showing the connection of the second substrate of the optical transmission module, the optical fiber, and the light-emitting device.

The through-holes 1171 are holes passing through the second substrate 1152 and communicating with the first surface 1152a and the second surface 1152b. The optical fiber 1121 is connected to the through-holes 1171. FIGS. 28 and 29 are cross-sectional views showing the optical fiber 1121 connected to the through-holes 1171. FIG. 28 is a cross-sectional view in the X-Y plane. FIG. 29 is a cross-sectional view in the Z-X plane. As shown in FIGS. 28 and 29, regarding the optical fiber 1121, core wires 1121a as core and cladding are covered with a covering layer 1121b made of a synthetic resin or the like.

As shown in FIGS. 28 and 29, the core wires 1121a are inserted into the through-holes 1171 from the side of the second surface 1152b. An identical number of through-holes 1171 to the number of core wires 1121a connected to the second substrate 1152 are provided. Here, it is assumed that the number of core wires 1121a connected to the second substrate 1152 is four and the number of through-holes 1171 is also four, though not limited thereto. Favorably, the through-hole 1171 has a diameter slightly larger than a diameter of the core wire 1121a and the diameter of the through-hole 1171 enables the position of the core wire 1121a to be fixed within the through-hole 1171.

The electrodes 1172 for the light-emitting device are electrically conductive and arranged on the first surface 1152a by plating, sputtering, vapor deposition, or the like. The number of electrodes 1172 for the light-emitting device and the arrangement thereof are not particularly limited. The wires 1173 are made of electrically conductive materials and electrically connect, in the surface of the first surface 1152a, the electrodes 1172 for the light-emitting device to the terminals 1174.

The terminals 1174 are electrically conductive and arranged on the first surface 1152a by plating, sputtering, vapor deposition, or the like. When the second substrate 1152 is connected to the first substrate 1151, the terminals 1174 come into contact with terminals (not shown) provided in the first substrate 1151 and electrically connect the first substrate 1151 to the electrodes 1172 for the light-emitting device. As shown in FIG. 25, the terminals 1174 can be arranged at peripheral cut-outs of the second substrate 1152.

Note that, if the cable 1012 includes an electrical signal line, the electrical signal line can also be connected to the second substrate 1152 and connected to the first substrate 1151 via the second substrate 1152.

The light-emitting device 1153 is mounted on the first surface 1152a and converts electrical signals into optical signals. As shown in FIGS. 28 and 29, the light-emitting device 1153 includes light-emitting portions 1153a. The light-emitting device 1153 is, for example, a VCSEL (Vertical Cavity Surface Emitting Laser) and can be a device in which the light-emitting portions 1153a and anode and cathode are arranged in an identical plane.

As shown in FIGS. 28 and 29, the light-emitting device 1153 can be joined to the electrodes 1172 for the light-emitting device through connection bumps B made of electrically conductive materials such as solder and gold, that is, mounted on the second substrate 1152 by flip-chip mounting. The light-emitting device 1153 is positioned in such a manner that the light-emitting portions 1153a are located at the centers of the through-holes 1171 and opposed to the core wires 1121a.

The light-emitting device 1153 is electrically connected to the second substrate 1152 via the electrodes 1172 for the light-emitting device and electrically connected to the IC 1154 for driving the light-emitting device via the first substrate 1151. The light-emitting device 1153 is driven by the IC 1154 for driving the light-emitting device and causes the light-emitting portions 1153a to emit light.

The IC 1154 for driving the light-emitting device is mounted on the first substrate 1151 and converts input electrical signals into those for driving the light-emitting device 1153 and outputs them to the light-emitting device 1153. The IC 1154 for driving the light-emitting device may be mounted on the first surface 1151a of the first substrate 1151 or may be mounted on the second surface 1151b.

The IC for control 1155 is mounted on the first substrate 1151 and controls various components installed in the optical transmission module 113, such as the IC 1154 for driving the light-emitting device. The IC for control 1155 may be mounted on the first surface 1151a or may be mounted on the second surface 1151b.

The passive devices 1156 are devices mounted on the first substrate 1151 and consume, store, or discharge supplied electric power. The passive devices 1156 are, for example, resistors, capacitors, or coils. The passive devices 1156 may be mounted on the first surface 1151a or may be mounted on the second surface 1151b.

Figure 30:
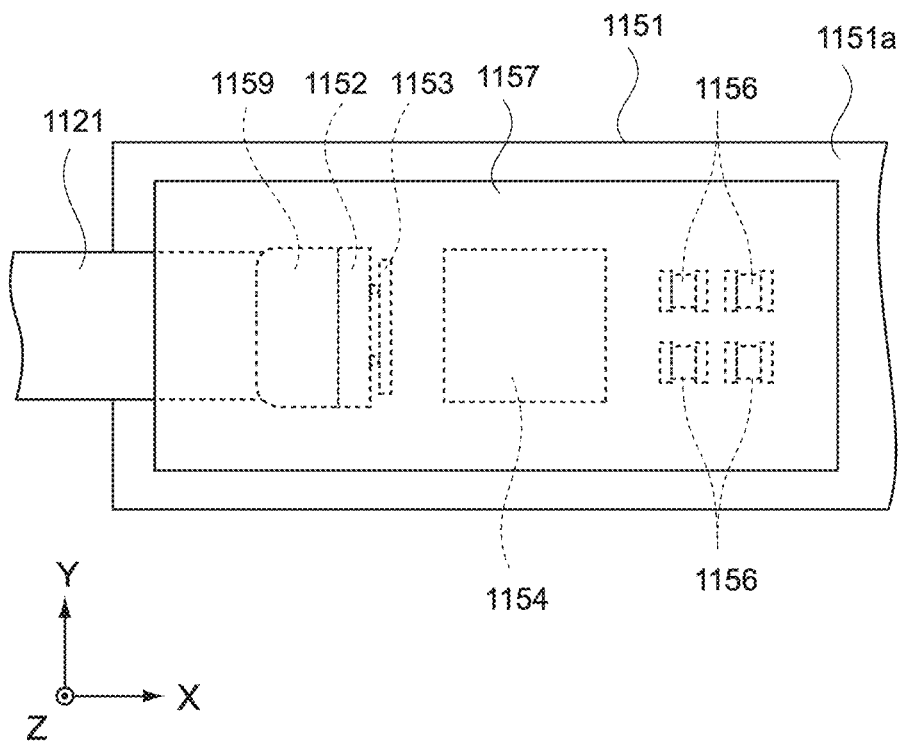
FIG. 30 A plan view of a first shield case of the optical transmission module.
Figure 31:
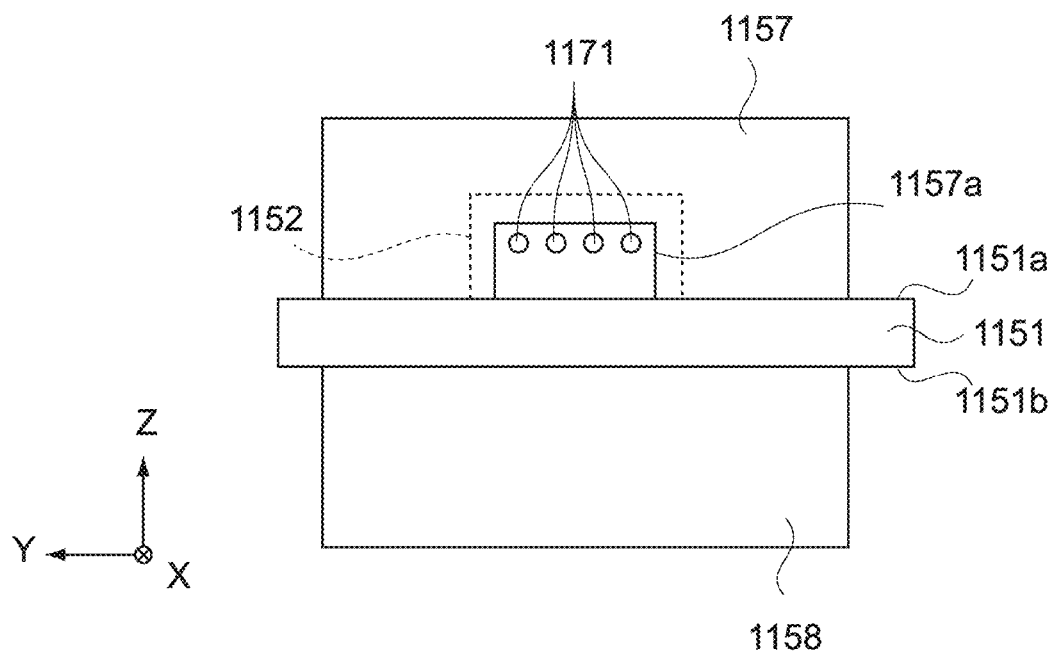
FIG. 31 A plan view of the first shield case and a second shield case of the optical transmission module.

The first shield case 1157 is joined to the first surface 1151a of the first substrate 1151. FIGS. 30 and 31 are plan views showing the first shield case 1157. FIG. 30 is a view as viewed from the side of the first surface 1151a of the first substrate 1151. FIG. 31 is a view as viewed from the side of the optical fiber 1121. Note that illustration of the optical fiber 1121 is omitted from FIG. 31.

As shown in these figures, the first shield case 1157 has a box-like shape including a rectangular top surface and side surfaces continuous with respective sides of the top surface and is joined to the first surface 1151a, surrounding the various components mounted on the first surface 1151a. Note that the shape of the first shield case 1157 is not particularly limited and can be a shape depending on an arrangement of the various components mounted on the first surface 1151a.

A housing space R1 (see FIG. 24) is formed by the first surface 1151a and the first shield case 1157. The various components such as the second substrate 1152, the light-emitting device 1153, the IC 1154 for driving the light-emitting device, and the passive devices 1156 which are mounted on the first surface 1151a are housed in the housing space R1.

Further, as shown in FIG. 31, an opening 1157a is provided in a side surface of the first shield case 1157. The opening 1157a is formed at a position facing the through-holes 1171 of the second substrate 1152. The optical fiber 1121 is inserted into the housing space R1 from an outside of the first shield case 1157 through the opening 1157a.

The first shield case 1157 can be made of a material having a high environment resistance, for example, metal or a synthetic resin. Although the first shield case 1157 can be joined to the first surface by soldering, adhesion with an adhesive, or the like, a joining method with which the sealing resin 1160 does not flow into the housing space R1 is desirable.

The second shield case 1158 is joined to the second surface 1151b of the first substrate 1151. The second shield case 1158 has a box-like shape similar to the first shield case 1157 and is joined to the second surface 1151b, surrounding the various components mounted on the second surface 1151b. Note that the shape of the second shield case 1158 is not particularly limited and can be a shape depending on an arrangement of the various components mounted on the second surface 1151b.

A housing space R2 (see FIG. 24) is formed by the second surface 1151b and the second shield case 1158. The various components such as the IC for control 1155 and the passive devices 1156 which are mounted on the second surface 1151b are housed in the housing space R2.

The second shield case 1158 can be made of a material having a high environment resistance, for example, metal or a synthetic resin. Although the second shield case 1158 can be joined to the first surface by soldering, adhesion with an adhesive, or the like, a joining method with which the sealing resin 1160 does not flow into the housing space R2 is desirable.

As shown in FIGS. 28 and 29, the adhesive resin 1159 is filled between the optical fiber 1121 and the second substrate 1152 and fixes the optical fiber 1121 and the second substrate 1152 to each other. The adhesive resin 1159 is made of a thermosetting resin or an ultraviolet curable resin and cured after the adhesive resin 1159 is filled between the optical fiber 1121 and the second substrate 1152.

The sealing resin 1160 is filled around the first substrate 1151, the first shield case 1157, and the second shield case 1158 and seals them. The sealing resin 1160 can be made of a synthetic resin having a low permeability to moisture, for example, an epoxy-based resin or a silicone-based resin.

Figure 32:
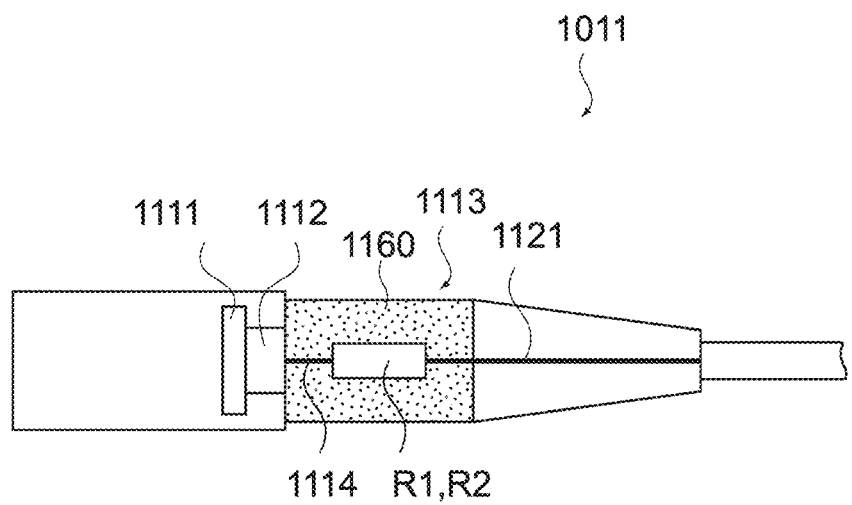
FIG. 32 A schematic view showing an arrangement of a sealing resin in the endoscope of the endoscope system according to the third embodiment of the present technology.
Figure 33:
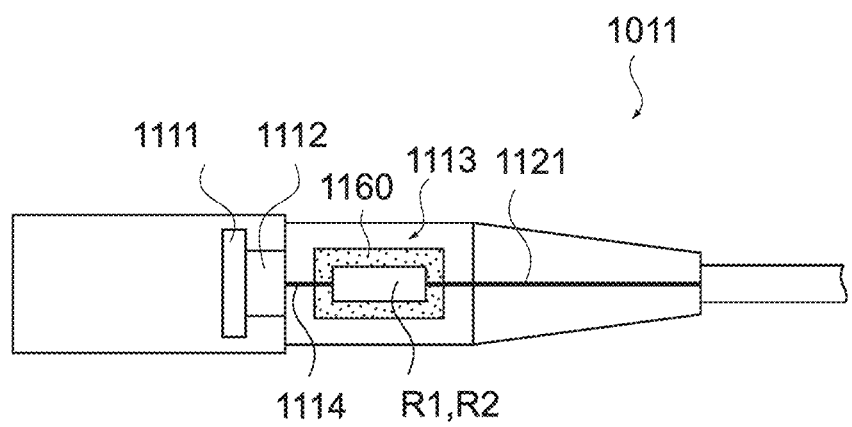
FIG. 33 A schematic view showing an arrangement of the sealing resin in the endoscope of the endoscope system.

FIGS. 32 and 33 are schematic views showing the insertion portion 1011. As shown in FIG. 32, the sealing resin 1160 can form a part of an exterior coating of the insertion portion 1011. Further, as shown in FIG. 33, the insertion portion 1011 may include an exterior coating member in addition to the sealing resin 1160 and the optical transmission module 1113 may be housed therein.

The optical transmission module 1113 has the configuration as described above. Note that the electrical signal line 1114 is connected to the first substrate 1151 via a connector (not shown).

[Operation of Endoscope]

When an image is picked up by the image pickup device 1111, the electrical signal processing unit 1112 subjects it to signal processing for transmission and generates electrical signals of the image. The electrical signal processing unit 1112 transmits the generated electrical signals to the optical transmission module 1113 via the electrical signal line 1114.

The electrical signals transmitted to the optical transmission module 1113 are input into the IC 1154 for driving the light-emitting device via the first substrate 1151. The IC 1154 for driving the light-emitting device converts the input electrical signals into signals for driving the light-emitting device 1153 and outputs them to the light-emitting device 1153 via the first substrate 1151 and the second substrate 1152.

The light-emitting device 1153 causes the light-emitting portions 1153a to emit light in accordance with the signals for driving supplied from the IC 1154 for driving the light-emitting device, in other words, converts electrical signals into optical signals. The light (optical signals) emitted from the light-emitting portions 1153a enters the core wires 1121a opposed thereto and is transferred to the connector 1013 via the optical fiber 1121 inside the cable 1012 and transmitted to the signal processing apparatus connected to the connector 1013.

[Effects of Endoscope]

By using the second substrate 1152, the optical transmission module 1113 optically couples the light-emitting device 1153 and the optical fiber 1121 to each other directly with a simple structure. With this, an optical coupling change is small with respect to a temperature cycle of an autoclave in sterilization treatment and stability is achieved. Further, the difference in coefficient of thermal expansion between the light-emitting device 1153 and the second substrate 1152 can be reduced. Thus, a high reliability of electrical connection can be ensured therebetween.

Further, as described above, the optical transmission module 1113 includes the sealing resin 1160. Also in a case where the optical transmission module 1113 is placed in the high temperature and high humidity environment, for example, in an autoclave, the sealing resin 1160 prevents moisture from infiltrating the housing space R1 and the housing space R2, and it becomes possible to protect the various components inside the housing spaces from the high temperature and high humidity environment. In particular, the light-emitting device 1153 is weak to the high temperature and high humidity environment. However, by protecting the light-emitting device 1153 from the high temperature and high humidity environment, it is possible to increase the reliability of the optical transmission module 1113.

[Manufacturing Method for Optical Transmission Module]

The optical transmission module 1113 can be manufactured as follows. First of all, the IC 1154 for driving the light-emitting device, the IC for control 1155, the passive devices 1156, and the like are mounted on the first substrate 1151 and the second substrate 1152 is joined thereto. Subsequently, the core wires 1121a of the optical fiber 1121 are inserted into the through-holes 1171 of the second substrate 1152 and the adhesive resin 1159 is filled between the second substrate 1152 and the optical fiber 1121. After that, the adhesive resin 1159 is cured by heating or irradiation with ultraviolet rays.

Subsequently, the first shield case 1157 and the second shield case 1158 are joined to the first substrate 1151, surrounding the various components. In addition, the sealing resin 1160 is filled around the first shield case 1157 and the second shield case 1158 for sealing them. The optical transmission module 1113 can thus be manufactured.

Modified Examples

Figure 34:
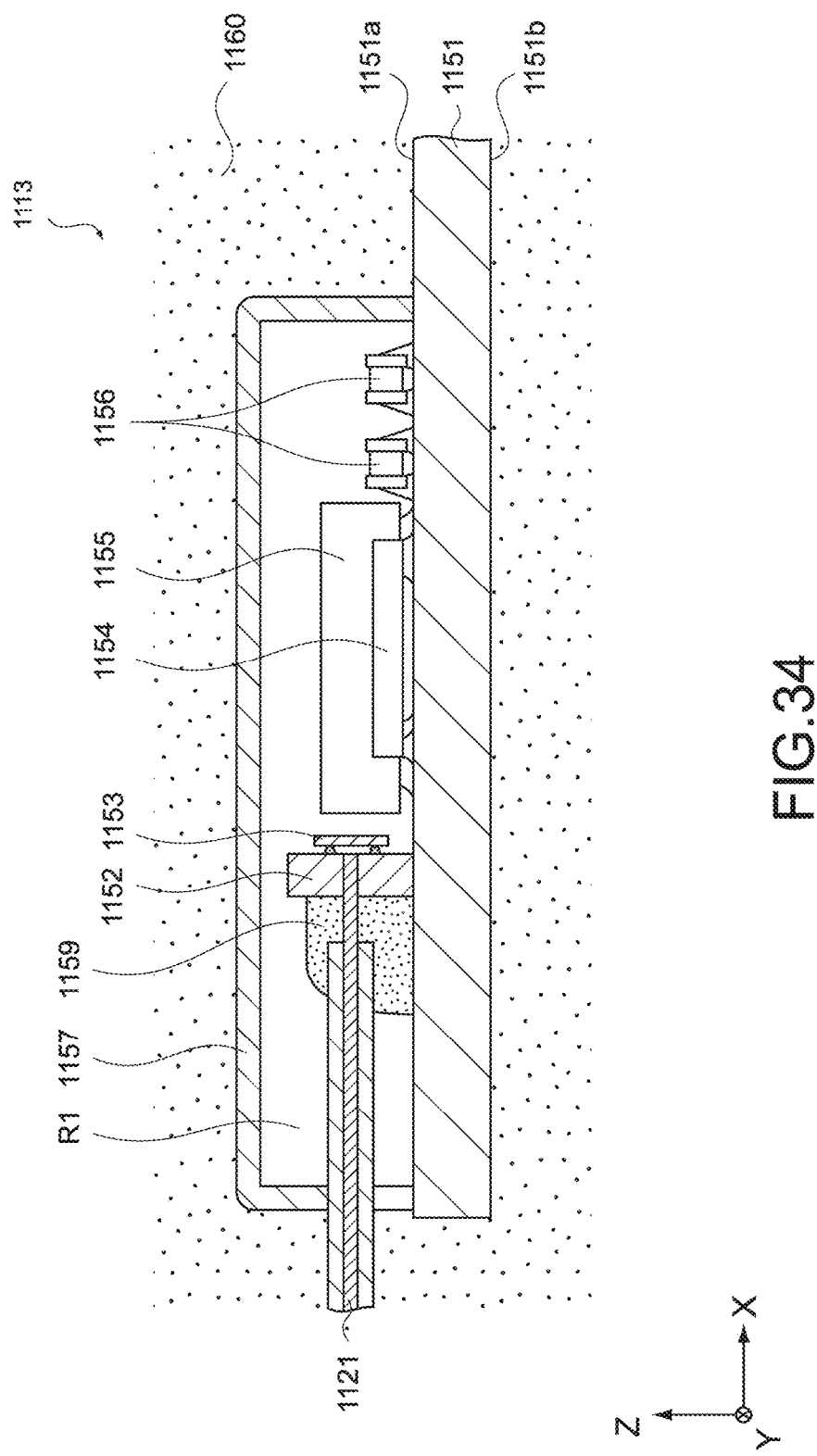
FIG. 34 A schematic view of an optical transmission module of an endoscope system according to a modified example of the third embodiment of the present technology.

In the above-mentioned embodiment, the various components are mounted on the first surface 1151a and the second surface 1151b of the first substrate 1151. However, the various components may be mounted on only either one of them. FIG. 34 is a schematic view showing the optical transmission module 1113 with the various components being mounted on only the first surface 1151a. As shown in the figure, in this case, the second shield case 1158 is not provided on the second surface and the second surface 1151b can be directly covered with the sealing resin 1160.

Further, the first shield case 1157 and the second shield case 1158 may be directly joined to the first substrate 1151 by soldering, adhesion, or the like as described above. However, the first shield case 1157 and the second shield case 1158 may be joined to the first substrate 1151 via a shield receiver.

Figure 35:
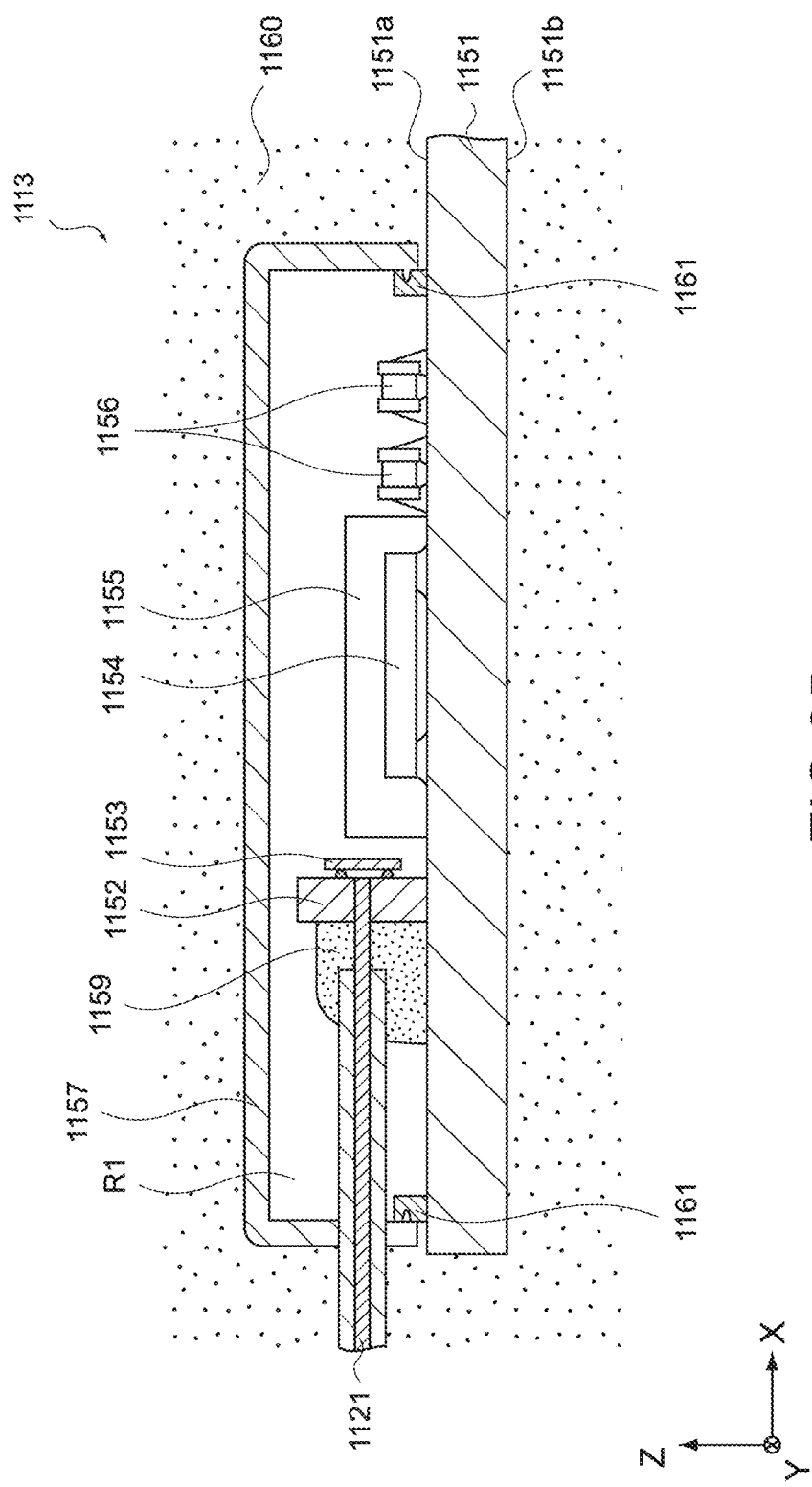
FIG. 35 A schematic view of an optical transmission module of an endoscope system according to a modified example of the third embodiment of the present technology.
Figure 36:
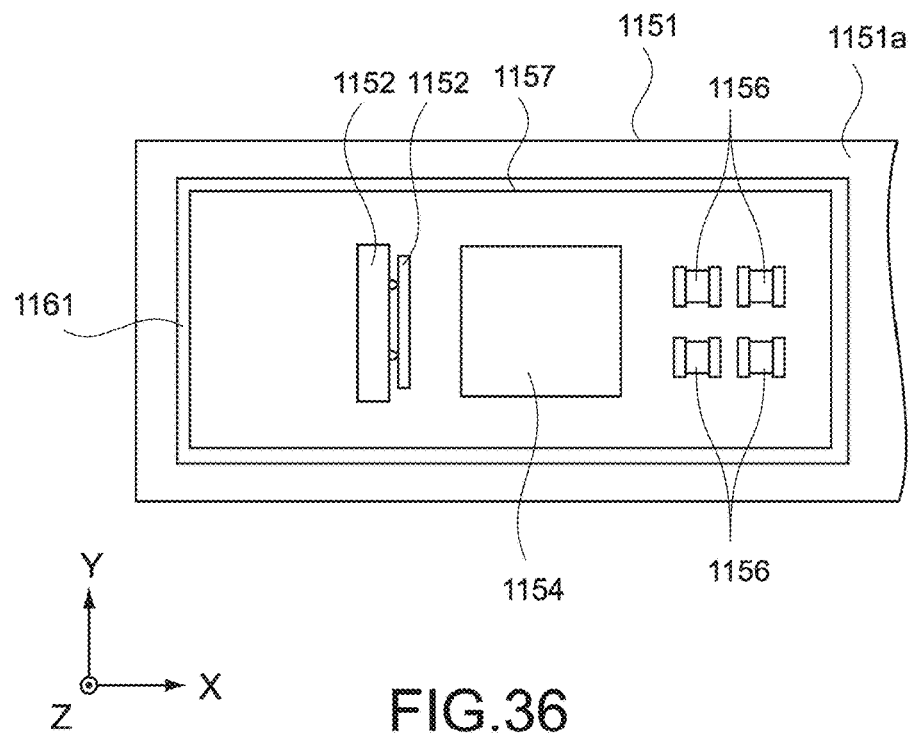
FIG. 36 A plan view showing an arrangement of a shield receiver in the optical transmission module.

FIG. 35 is a cross-sectional view showing an optical transmission module 1113 including a shield receiver 1161. FIG. 36 is a plan view of the optical transmission module 1113. Note that illustration of the sealing resin 1160, the first shield case 1157, the optical fiber 1121, and the adhesive resin 1159 is omitted from FIG. 36.

As shown in these figures, the shield receiver 1161 is, on the first surface 1151*a*, arranged surrounding the various components mounted on the first surface 1151*a*.

Figure 37:
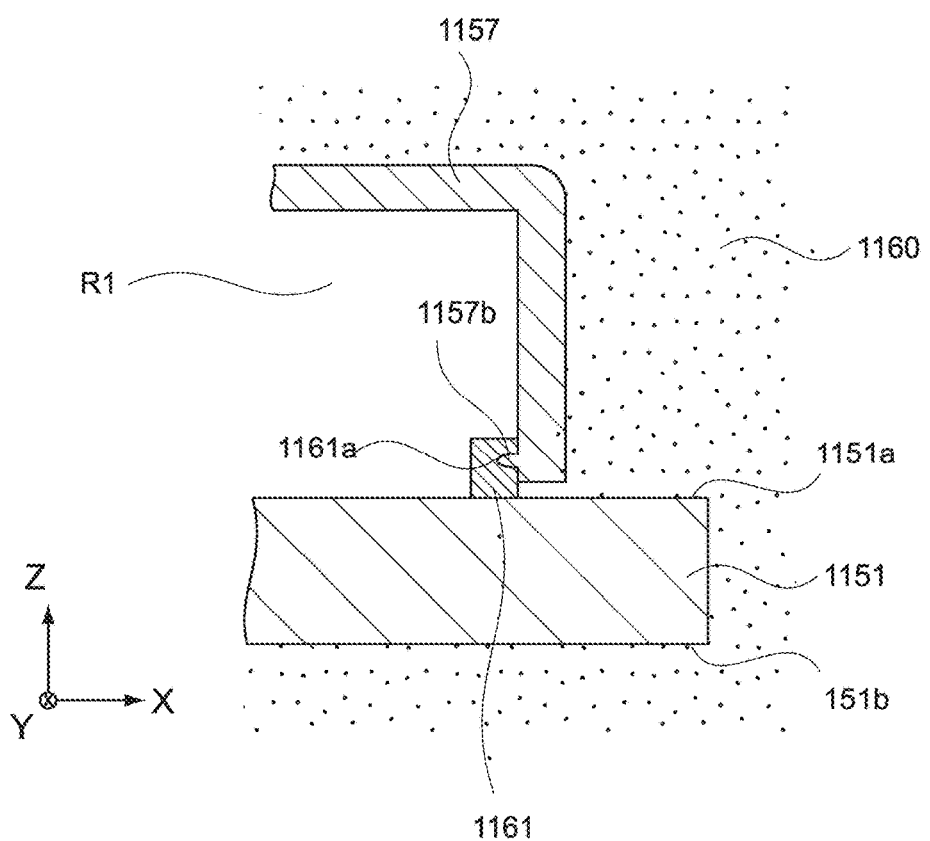
FIG. 37 A schematic view showing joining of the shield case and the shield receiver in the optical transmission module.

FIG. 37 is an enlarged view showing the shield receiver 1161. As shown in the figure, the shield receiver 1161 includes a recess portion 1161*a* and the first shield case 1157 includes a convex portion 1157*b*. The first shield case 1157 is joined to the first surface 1151*a* by the convex portion 1157*b* being fitted in the recess portion 1170*a*. Note that the shield receiver 1161 may be provided with the convex portion and the first shield case 1157 may be provided with the recess portion.

Figure 38:
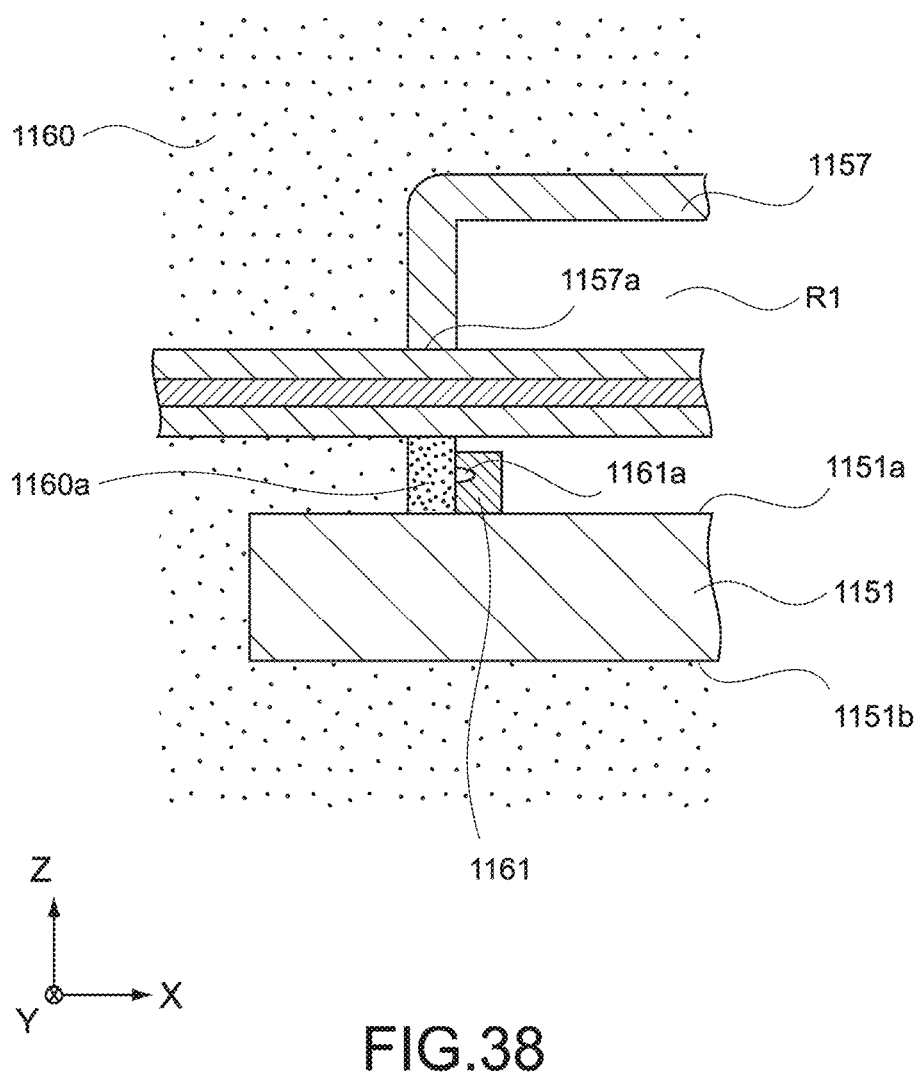
FIG. 38 A schematic view showing a cover portion in the optical transmission module.

On the other hand, the first shield case 1157 is provided with the opening 1157*a* (see FIG. 31) into which the optical fiber 1121 is inserted. In the opening 1157*a*, the shield receiver 1161 functions as a barrier that prevents the sealing resin 1160 from flowing into the housing space R1. FIG. 38 is an enlarged view showing the shield receiver 1161 in the opening 1157*a*.

When the sealing resin 1160 is filled around the first shield case 1157, it is possible to form a cover portion 1160*a* between the opening 1157*a* and the shield receiver 1161 as shown in the figure. The cover portion 1160*a* is filled without flowing into the housing space R1. The cover portion 1160*a* may be made of a synthetic resin different from the sealing resin 1160 or may be made of a synthetic resin identical to the sealing resin 1160. However, a synthetic resin having a high viscosity is favorable. The opening 1157*a* is closed by the cover portion 1160*a*, and hence it is possible to reliably prevent the sealing resin 1160 from flowing into the housing space R1.

Fourth Embodiment

An endoscope system according to a fourth embodiment of the present technology will be described.

[Configuration of Endoscope System]

Figure 39:
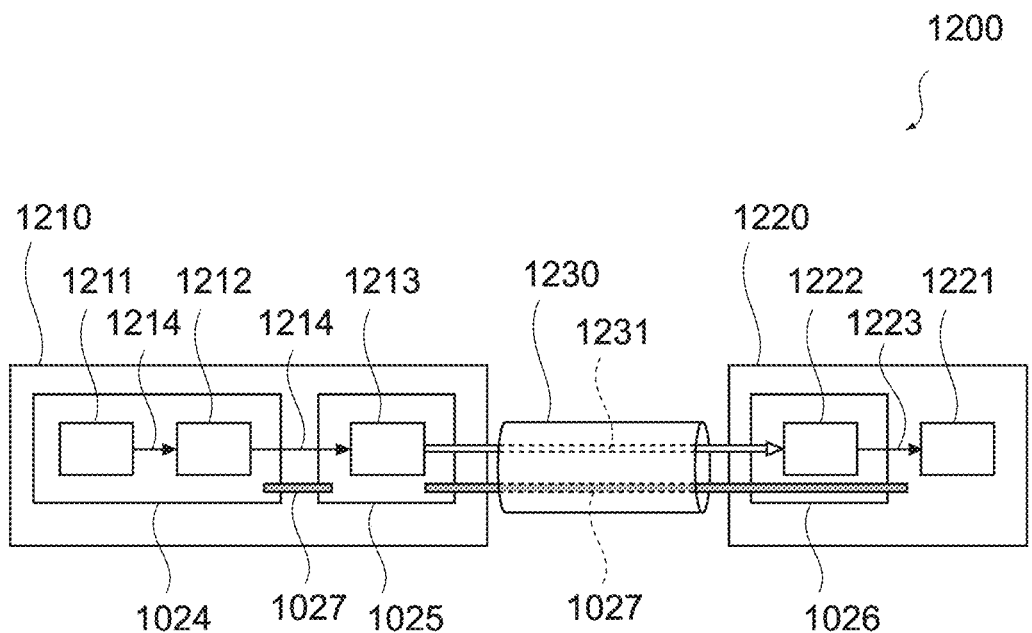
FIG. 39 A schematic view of an endoscope system according to a fourth embodiment of the present technology.

FIG. 39 is a block diagram showing a configuration of an endoscope system 1200 according to this embodiment. As shown in the figure, the endoscope system 1200 includes an endoscope 1210, an information processing apparatus 1220, and a cable 1230.

The endoscope 1210 includes a camera head 1024 and an optical transmission module 1025.

The camera head 1024 includes an image pickup device 1211 and an electrical signal processing unit 1212. The optical transmission module 1025 includes a photoelectric conversion device 1213. The image pickup device 1211, the electrical signal processing unit 1212, and the photoelectric conversion device 1213 are connected to one another through electrical signal lines 1214. The photoelectric conversion device 1213 is connected to an optical fiber 1231.

The image pickup device 1211 is a CCD image sensor or a CMOS image sensor and picks up an image via an image pickup optical system (not shown) and generates electrical signals of the image. The image pickup device 1211 outputs the generated electrical signals to the electrical signal processing unit 1212 via the electrical signal line 1214.

The electrical signal processing unit 1212 subjects the electrical signals supplied from the image pickup device 1211 to signal processing for transmission and outputs them to the photoelectric conversion device 1213 via the electrical signal line 1214.

The photoelectric conversion device 1213 converts the electrical signals supplied from the electrical signal processing unit 1212 into optical signals and causes them to enter the optical fiber 1231.

The information processing apparatus 1220 includes an optical transmission module 1026 and an electrical signal processing unit 1221. The optical transmission module 1026 includes a photoelectric conversion device 1222. The photoelectric conversion device 1222 is connected to the optical fiber 1231. The photoelectric conversion device 1222 and the electrical signal processing unit 1221 are connected to each other through an electrical signal line 1223.

The photoelectric conversion device 1222 converts the optical signals emitted from the optical fiber 1231 into electrical signals and outputs them to the electrical signal processing unit 1221 via the electrical signal line 1223.

The electrical signal processing unit 1221 subjects the electrical signals supplied from the photoelectric conversion device 1222 to signal processing for image generation. The electrical signal processing unit 1221 supplies the generated electrical signals to a processor for image generation (not shown) or outputs them to another information processing apparatus.

Heat conducting wires 1027 are arranged between the camera head 1024 and the optical transmission module 1025 and between the optical transmission module 1025 and the optical transmission module 1026. The heat conducting wires 1027 are made of materials having a high thermal conductivity, such as metal.

The cable 1230 connects the endoscope 1210 and the information processing apparatus 1220 to each other. The cable 1230 includes the optical fiber 1231 and the heat conducting wire 1027.

[Effects of Endoscope System]

As described above, the heat conducting wires 1027 are arranged between the camera head 1024 and the optical transmission module 1025 and between the optical transmission module 1025 and the information processing apparatus 1220, respectively. With this, heat generated in the camera head 1024 is transferred to the information processing apparatus 1220 via the optical transmission module 1025 and the cable 1230 and dissipated.

At this time, if the power consumption of the optical transmission module 1025 is larger than that of the camera head 1024, the heat cannot pass through the optical transmission module 1025. The present technology is to design the system in order to ensure that the power consumption of the optical transmission module 1025 is smaller than the power consumption of the camera head 1024. For example, in order to set the power consumption of the optical transmission module 1025 to be ½ or less of that of the camera head 1024, devises of lowering the transmission speed of signal lines and making them parallel to thereby reduce the power consumption are conceivable, for example.

Fifth Embodiment

An endoscope system according to a fifth embodiment of the present technology will be described.

[Configuration of Endoscope System]

Figure 40:
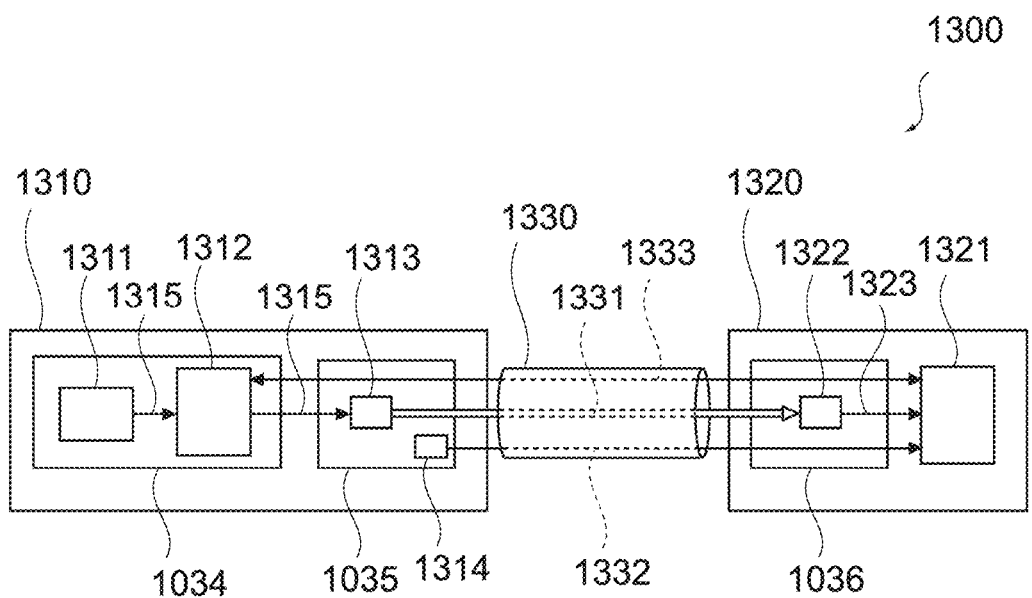
FIG. 40 A schematic view of an endoscope system according to a fifth embodiment of the present technology.

FIG. 40 is a block diagram showing a configuration of an endoscope system 1300 according to this embodiment. As shown in the figure, the endoscope system 1300 includes an endoscope 1310, an information processing apparatus 1320, and a cable 1330.

The endoscope 1310 includes a camera head 1034 and an optical transmission module 1035.

The camera head 1034 includes an image pickup device 1311 and an electrical signal processing unit 1312. The optical transmission module 1035 includes a photoelectric conversion device 1313 and a controller 1314. The image pickup device 1311, the electrical signal processing unit 1312, and the photoelectric conversion device 1313 are connected to one another through electrical signal lines 1315. The photoelectric conversion device 1313 is connected to an optical fiber 1331. Further, the controller 1314 is connected to the information processing apparatus 1320 via an electrical signal line 1332 and the electrical signal processing unit 1312 is connected to the information processing apparatus 1320 via an electrical signal line 1333.

The image pickup device 1311 is a CCD image sensor or a CMOS image sensor and picks up an image via an image pickup optical system (not shown) and generates electrical signals of the image. The image pickup device 1311 outputs the generated electrical signals to the electrical signal processing unit 1312 via the electrical signal line 1315.

The electrical signal processing unit 1312 subjects the electrical signals supplied from the image pickup device 1311 to signal processing for transmission and outputs them to the photoelectric conversion device 1313 via the electrical signal line 1315.

The photoelectric conversion device 1313 converts the electrical signals supplied from the electrical signal processing unit 1312 into optical signals and causes them to enter the optical fiber 1331. The photoelectric conversion device 1313 can include a laser light source that generates optical signals.

The controller 1314 incorporates therein a micro processor that detects a driving state and a driving cumulative time of the photoelectric conversion device 1313 and a memory. The controller 1314 stores histories in which the photoelectric conversion device 1313 has actually been used (hereinafter, use histories). The controller 1314 outputs the use histories to the information processing apparatus 1320 via the electrical signal line 1332.

The information processing apparatus 1320 includes an optical transmission module 1036 and an electrical signal processing unit 1321. The optical transmission module 1036 includes a photoelectric conversion device 1322. The photoelectric conversion device 1322 is connected to the optical fiber 1331. The photoelectric conversion device 1322 and the electrical signal processing unit 1321 are connected to each other through an electrical signal line 1323. Further, the electrical signal line 1332 and the electrical signal line 1333 are connected to the electrical signal processing unit 1321.

The photoelectric conversion device 1322 converts the optical signals emitted from the optical fiber 1331 into electrical signals and outputs them to the electrical signal processing unit 1321 via the electrical signal line 1323.

The electrical signal processing unit 1321 subjects the electrical signals supplied from the photoelectric conversion device 1322 to signal processing for image generation. The electrical signal processing unit 1321 supplies the generated electrical signals to a processor for image generation (not shown) or outputs them to another information processing apparatus.

Further, the electrical signal processing unit 1321 acquires the use histories output from the controller 1314 via the electrical signal line 1332.

The cable 1330 connects the endoscope 1310 and the information processing apparatus 1320 to each other. The cable 1330 includes the optical fiber 1331, the electrical signal line 1332, and the electrical signal line 1333.

[Effects of Endoscope System]

The lifetime of the laser light source installed in the photoelectric conversion device 1313 depends on environments in which it is driven, and hence there is a fear that communication errors may occur when the lifetime of the laser light source ends. As described above, the endoscope system 1300 has the configuration in which the controller 1314 supplies the use histories of the photoelectric conversion device 1313 to the electrical signal processing unit 1321. Therefore, the information processing apparatus 1320 can know the lifetime of the laser light source and it is possible to prevent communication errors before they happen.

It should be noted that the present technology may also take the following configurations.

(1)

An optical connector, including:

a lens support including a through-hole;

a fiber ferrule to which an optical fiber is connected and which is press-fitted in the through-hole;

a lens inserted into the through-hole; and a lens retainer which is press-fitted in the lens support and sandwiches the lens between the lens retainer and the fiber ferrule.

(2)

The optical connector according to (1), further including a connector frame in which the lens support is press-fitted and which is fitted in/on a connection target connector.

(3)

The optical connector according to (1), in which the lens support is a connector frame fitted in/on a connection target connector.

(4)

The optical connector according to any one of (1) to (3), in which the lens retainer is made of a material not having light transmissivity and includes an opening that permits emitted light of the lens to pass therethrough.

(5)

The optical connector according to any one of (1) to (4), in which the lens support includes a recess portion that communicates with the through-hole, and the lens retainer is press-fitted in the recess portion.

(6)

An optical connector set, including:

a first optical connector including a first lens support including a first through-hole, a first fiber ferrule to which a first optical fiber is connected and which is press-fitted in the first through-hole, a first lens which is inserted into the first through-hole and which emitted light of the first optical fiber enters, and a first lens retainer which is press-fitted in the first lens support and sandwiches the first lens between the first lens retainer and the first fiber ferrule; and a second optical connector including a second lens support including a second through-hole, a second fiber ferrule to which a second optical fiber is connected and which is press-fitted in the second through-hole, a second lens which is inserted into the second through-hole and causes emitted light to enter the second optical fiber, and a second lens retainer which is press-fitted in the second lens support and sandwiches the second lens between the second lens retainer and the second fiber ferrule, in which the first optical connector and the second optical connector are attachable/detachable, and emitted light of the first lens enters the second lens once the first optical connector and the second optical connector are connected to each other.

(7)

An image pickup unit, including:
an image pickup portion including
an image pickup device, and
a photoelectric conversion device that converts an output signal of the image pickup device into an optical signal;
a cable connected to the photoelectric conversion device and including an optical fiber which the optical signal enters; and
an optical connector including
a lens support including a through-hole,
a fiber ferrule to which the optical fiber is connected and which press-fitted in the through-hole,
a lens which is inserted into the through-hole and which emitted light of the optical fiber enters, and
a lens retainer which is press-fitted in the lens support and sandwiches the lens between the lens retainer and the fiber ferrule.

(8)

An image pickup system, including:
an image pickup unit; and
a main body unit, in which
the image pickup unit includes
an image pickup portion including
an image pickup device, and
a first photoelectric conversion device that converts an output signal of the image pickup device into an optical signal,
a cable connected to the first photoelectric conversion device and including a first optical fiber which the optical signal enters, and
a first optical connector including
a first lens support including a first through-hole,
a first fiber ferrule to which a first optical fiber is connected and which is press-fitted in the first through-hole,
a first lens which is inserted into the first through-hole and which emitted light of the first optical fiber enters, and
a first lens retainer which is press-fitted in the first lens support and sandwiches the first lens between the first lens retainer and the first fiber ferrule, and
the main body unit includes
a second optical connector which is detachably connected to the first optical connector and to which the optical signal is transferred, and
a second photoelectric conversion device that converts the optical signal into an electrical signal.

(9)

The image pickup system according to (8), in which
the second optical connector includes
a second lens support including a second through-hole,
a second fiber ferrule to which a second optical fiber is connected and which is press-fitted in the second through-hole,
a second lens which is inserted into the second through-hole and causes emitted light to enter the second optical fiber, and a second lens retainer which is press-fitted in the second lens support and sandwiches the second lens between the second lens retainer and the second fiber ferrule, and emitted light of the first lens enters the second lens once the second optical connector is connected to the first optical connector.

(10)

An optical transmission module, including:
a first substrate;
a second substrate which is fixed to the first substrate and includes a wire electrically connected to the first substrate and a through-hole;
an optical fiber inserted into the through-hole and fixed to the second substrate through a first synthetic resin;
a light-emitting device which is mounted on the second substrate, includes a light-emitting portion opposed to an end portion of the optical fiber, and is electrically connected to the wire; and
a shield case which is joined to the first substrate and forms a housing space surrounding components installed in the first substrate, the components including the second substrate and the light-emitting device.

(11)

The optical transmission module according to (10), further including
a sealing resin which is made of a second synthetic resin and seals the shield case.

(12)

The optical transmission module according to (10) or (11), in which
The optical transmission module according to claim 10, in which
the light-emitting device is mounted on the second substrate through a connection bump.

(13)

The optical transmission module according to any one of (10) to (12), in which
the first substrate and the second substrate are made of silicon, quartz, glass, ceramics, or organic materials.

(14)

The optical transmission module according to any one of (10) to (12), in which
the connection bump is made of solder or gold.

(15)

The optical transmission module according to any one of (10) to (14), in which
the second synthetic resin is an epoxy-based resin or a silicone-based resin.

(16)

The optical transmission module according to any one of (10) to (15), in which
the shield case includes an opening, and
the optical fiber is inserted into the housing space through the opening, the optical transmission module further including:
a shield receiver which is arranged on the first substrate and in/on which the shield case is fitted, the shield receiver being arranged surrounding the components installed in the first substrate; and
a cover portion which is made of the second synthetic resin or a third synthetic resin and closes a gap between the opening and the shield receiver.

REFERENCE SIGNS LIST

10, 20 . . . endoscope system
11, 21 . . . image pickup unit 12, 22 . . . main body unit
13, 23 . . . image pickup distal end
14, 24, 17, 27 . . . cable
15, 25 . . . plug-side connector
16, 26 . . . main body
18, 28 . . . receptor-side connector
151, 251, 181, 281 . . . connector frame
152, 182 . . . lens holder
153, 183, 253, 283 . . . lens
154, 184, 254, 284 . . . lens retainer
1100, 1200, 1300 . . . endoscope system
1110 . . . endoscope
1113 . . . optical transmission module
1121 . . . optical fiber
1151 . . . first substrate
1152 . . . second substrate
1153 . . . light-emitting device
1157 . . . first shield case
1158 . . . second shield case
1159 . . . adhesive resin
1160 . . . sealing resin
1171 . . . through-hole
1172 . . . electrode for light-emitting device
1173 . . . wire

The invention claimed is:

1. An optical connector, comprising:
a lens support including a through-hole and a recess portion;
a fiber ferrule connected to an optical fiber, wherein the fiber ferrule is press-fitted in the through-hole;
a lens inserted into the through-hole; and
a lens retainer press-fitted in the recess portion of the lens support, wherein
the lens is between the lens retainer and the fiber ferrule,
the lens retainer includes an opening,
the lens faces the opening of the lens retainer, and
a diameter of the opening is smaller than a diameter of the lens.

2. The optical connector according to claim 1, further comprising a connector frame in which the lens support is press-fitted, wherein the connector frame is one of in a connection target connector or on the connection target connector.

3. The optical connector according to claim 1, wherein the lens support is a connector frame one of in a connection target connector or on the connection target connector.

4. The optical connector according to claim 1, wherein
the lens retainer includes a material not having light transmissivity,
the lens is configured to emit light, and
the opening permits the emitted light to pass therethrough.

5. An optical connector set, comprising:
a first optical connector including:
a first lens support including a first through-hole and a recess portion;
a first fiber ferrule connected to a first optical fiber, wherein the first fiber ferrule is press-fitted in the first through-hole;
a first lens inserted into the first through-hole, wherein the first lens is configured to receive light emitted from the first optical fiber; and
a first lens retainer press-fitted in the recess portion of the first lens support, wherein
the first lens is between the first lens retainer and the first fiber ferrule,
the first lens retainer includes an opening,
the first lens faces the opening of the first lens retainer, and
a diameter of the opening is smaller than a diameter of the first lens; and
a second optical connector including:
a second lens support including a second through-hole;
a second fiber ferrule connected to a second optical fiber, wherein the second fiber ferrule is press-fitted in the second through-hole;
a second lens inserted into the second through-hole, wherein the second lens is configured to:
receive the light from the first lens based on a connection of the first optical connector with the second optical connector; and
cause the light received from the first lens to enter the second optical fiber; and
a second lens retainer press-fitted in the second lens support, wherein
the second lens is between the second lens retainer and the second fiber ferrule, and
the first optical connector is attachable to the second optical connector.

6. An image pickup unit, comprising:
an image pickup portion including:
an image pickup device configured to output an output signal; and
a photoelectric conversion device configured to convert the output signal into an optical signal;
a cable connected to the photoelectric conversion device, wherein
the cable includes an optical fiber configured to:
receive the optical signal; and
output the received optical signal; and
an optical connector including:
a lens support including a through-hole;
a fiber ferrule connected to the optical fiber, wherein the fiber ferrule is press-fitted in the through-hole;
a lens inserted into the through-hole, wherein the lens is configured to receive the optical signal output by the optical fiber; and
a lens retainer press-fitted in the lens support, wherein the lens is between the lens retainer and the fiber ferrule.

7. An image pickup system, comprising:
an image pickup unit; and
a main body unit, wherein
the image pickup unit includes:
an image pickup portion including:
an image pickup device configured to output an output signal; and
a first photoelectric conversion device configured to convert the output signal into an optical signal;
a cable connected to the first photoelectric conversion device, wherein the cable includes a first optical fiber configured to:
receive the optical signal; and
output the received optical signal; and
a first optical connector including:
a first lens support including a first through-hole;
a first fiber ferrule connected to the first optical fiber, wherein the first fiber ferrule is press-fitted in the first through-hole;
a first lens inserted into the first through-hole, wherein the first lens is configured to receive the optical signal output by the first optical fiber; and a first lens retainer press-fitted in the first lens support, wherein the first lens is between the first lens retainer and the first fiber ferrule, and the main body unit includes:
a second optical connector detachably connected to the first optical connector, wherein the second optical connector is configured to receive the optical signal from the first optical connector; and
a second photoelectric conversion device configured to:
receive the optical signal from the second optical connector; and
convert the optical signal into an electrical signal.

8. The image pickup system according to claim 7, wherein the second optical connector includes:
a second lens support including a second through-hole;
a second fiber ferrule connected to a second optical fiber, wherein the second fiber ferrule is press-fitted in the second through-hole;
a second lens inserted into the second through-hole, wherein the second lens is configured to:
receive the optical signal from the first lens based on a connection of the second optical connector with the first optical connector; and
cause the optical signal to enter the second optical fiber; and
a second lens retainer press-fitted in the second lens support, wherein
the second lens is between the second lens retainer and the second fiber ferrule.

9. An optical connector, comprising:
a lens support including a through-hole;
a fiber ferrule connected to an optical fiber, wherein the fiber ferrule is press-fitted in the through-hole;
a lens inserted into the through-hole;
a lens retainer press-fitted in the lens support, wherein
the lens is between the lens retainer and the fiber ferrule,
the lens retainer includes an opening,
the lens faces the opening of the lens retainer, and
a diameter of the opening is smaller than a diameter of the lens; and
a connector frame in which the lens support is press-fitted, wherein the connector frame is one of in a connection target connector or on the connection target connector.

* * * * *